US008178056B2

(12) United States Patent
Yokoyama

(10) Patent No.: US 8,178,056 B2
(45) Date of Patent: May 15, 2012

(54) BIOCHEMICAL REACTION CARTRIDGE AND BIOCHEMICAL TREATMENT EQUIPMENT SYSTEM

(75) Inventor: Daisuke Yokoyama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 125 days.

(21) Appl. No.: 11/265,457

(22) Filed: Nov. 1, 2005

(65) Prior Publication Data
US 2006/0093517 A1 May 4, 2006

(30) Foreign Application Priority Data

Nov. 2, 2004 (JP) ................................. 2004-319221

(51) Int. Cl.
*G01N 21/01* (2006.01)
(52) U.S. Cl. ........ 422/404; 422/400; 422/402; 422/403; 436/86; 436/94; 436/164; 436/172; 435/287.2; 435/288.4
(58) Field of Classification Search .............. 422/58, 422/63, 102; 435/6, 287.2, 288.4; 436/43, 436/172
See application file for complete search history.

(56) References Cited

U.S. PATENT DOCUMENTS

| 5,445,934 | A | 8/1995 | Fodor et al. |
| 5,474,796 | A * | 12/1995 | Brennan ...................... 427/2.13 |
| 2003/0235520 | A1 * | 12/2003 | Shea et al. ..................... 422/102 |
| 2004/0224339 | A1 * | 11/2004 | Numajiri et al. .................. 435/6 |
| 2004/0241659 | A1 * | 12/2004 | Cox et al. .......................... 435/6 |
| 2005/0227274 | A1 * | 10/2005 | Takahashi .......................... 435/6 |
| 2006/0134704 | A1 | 6/2006 | Muraguchi et al. |

FOREIGN PATENT DOCUMENTS

| JP | 2832117 | 9/1998 |
| JP | 11-509094 | 8/1999 |
| JP | 2000-274375 | 10/2000 |
| JP | 2004-173681 | 6/2004 |

OTHER PUBLICATIONS

Lueking, et al, "Protein Microarrays for Gene Expression and Antibody Screening", Analytical Biochemisty 270, pp. 103-111 (1999).
Reason of Refusal With Respect to Corresponding JP 2004-319221 (dated Nov. 29, 2006) and English Translation.
Additional Statement of Relevance for Reason of Refusal With Respect to Corresponding JP 2004-319221.

* cited by examiner

*Primary Examiner* — P. Kathryn Wright
(74) *Attorney, Agent, or Firm* — Canon USA Inc. IP Division

(57) ABSTRACT

There is provided a biochemical reaction cartridge comprising at least one chemical reaction chamber that accommodates a solution for biochemically treating a sample, a reaction chamber for performing detection reaction of a target substance in the biochemically treated sample, and a detection reaction information fetching section for fetching information on whether or not the detection reaction is performed, wherein the biochemical reaction cartridge is provided with a covering unit that can cover and expose at least the reaction information fetching section.

5 Claims, 14 Drawing Sheets

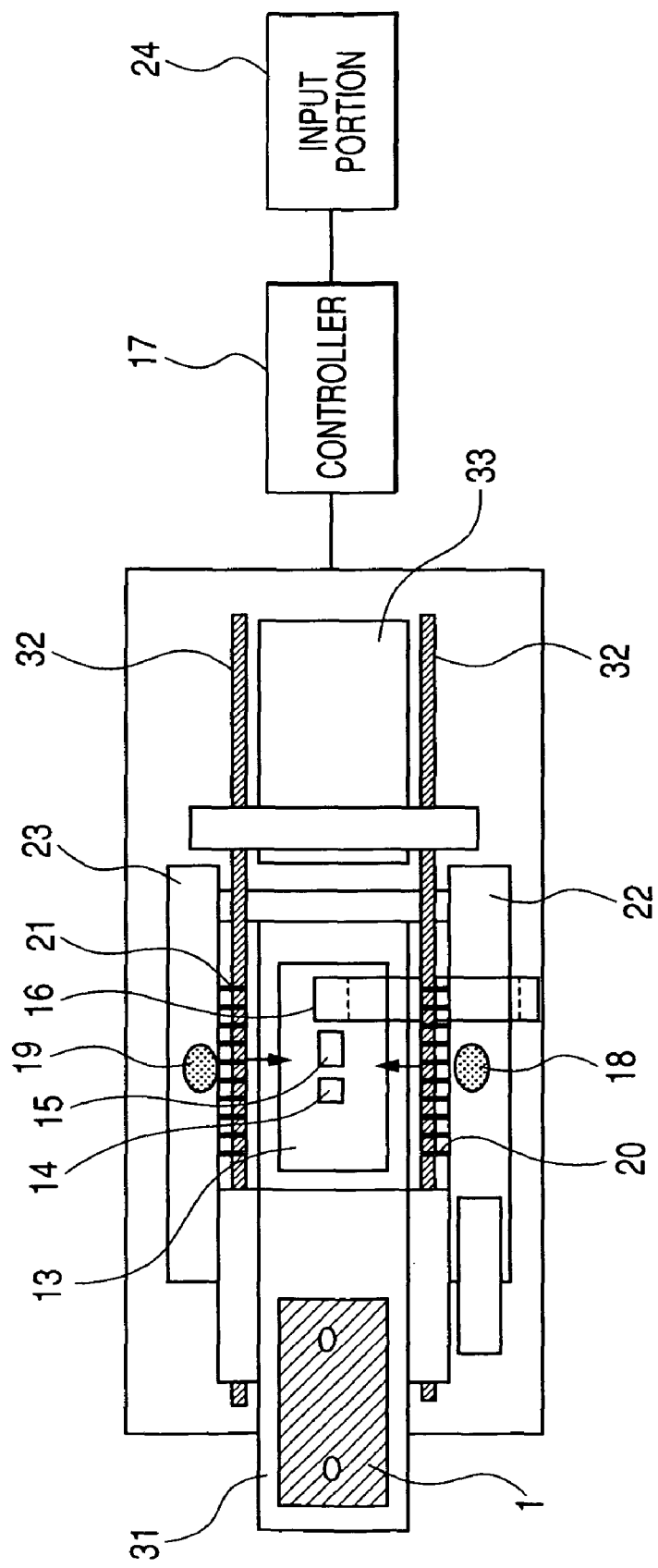

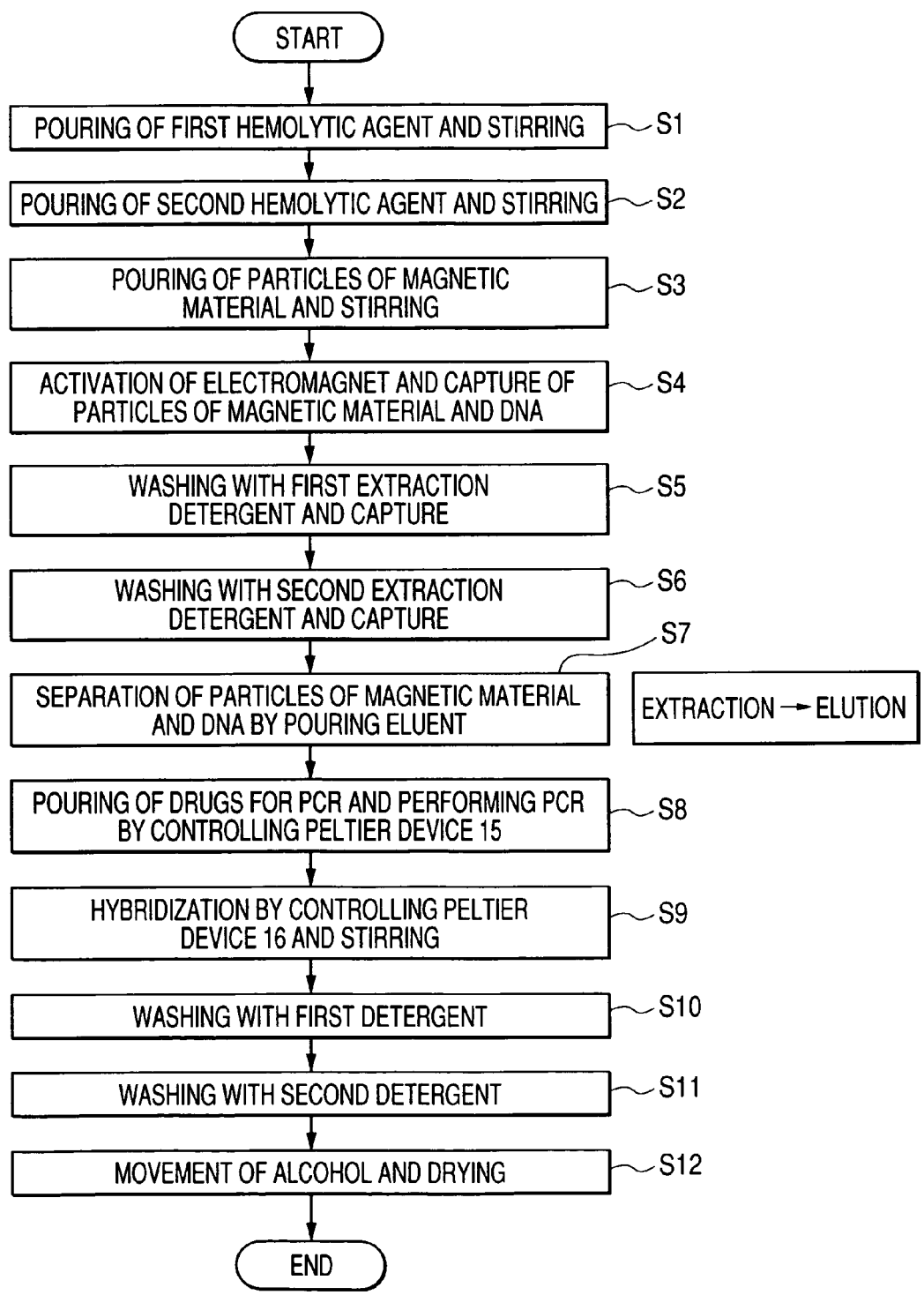

BIOCHEMICAL REACTION CARTRIDGE AND BIOCHEMICAL TREATMENT EQUIPMENT SYSTEM

BACKGROUND OF THE INVENTION

1. Field of the Invention

The present invention relates to equipment that analyzes cells, microorganisms, chromosomes, nucleic acids or the like in samples by use of biochemical reaction such as antigen-antibody reaction or nucleic acid hybridization, and to a biochemical treatment equipment system comprising a biochemical reaction cartridge used integrally with the equipment.

2. Related Background Art

A vast majority of analyzers for analyzing samples such as blood use an immunological method that utilizes antigen-antibody reaction or a method that utilizes nucleic acid hybridization. For example, the analyzers use a protein such as an antibody or an antigen specifically binding to a substance to be detected or a single-stranded nucleic acid as a probe, which is in turn immobilized on the surface of a solid phase such as fine particles, beads or glass plates and subjected to antigen-antibody reaction or nucleic acid hybridization with the substance to be detected. Then, a labeled substance having specific interaction, for example, a labeled antibody or antigen or a labeled nucleic acid, which carries a labeling material with high detection sensitivity such as enzymes, fluorescent materials or luminescent materials, is used to detect the presence or absence of the substance to be detected or quantify the substance to be detected, by detecting an antigen-antibody complex or a double-stranded nucleic acid.

For example, U.S. Pat. No. 5,445,934 discloses, as a modification of these techniques, a so-called DNA microarray where a large number of DNA (deoxyribonucleic acid) probes with a different base sequence from one another are arrayed on a substrate.

Alternatively, Anal. Biochem., 270 (1), p. 103-111, 1999 discloses a method of fabricating a protein array structurally similar to a DNA microarray, in which plural types of proteins are arranged on a membrane filter. As described above, the use of a DNA microarray, a protein array and so on has allowed the examination of a very large number of items at a time.

In various methods of sample analysis, a disposable biochemical reaction cartridge that internally performs necessary reaction is also proposed for the purpose of reducing contamination by samples, improving reaction efficiency, miniaturizing equipment, simplifying procedures, etc. For example, National Publication of International Patent Application No. H11-509094 discloses a biochemical reaction cartridge capable of extraction or amplification of DNA in a sample or reaction such as hybridization in the interior of the cartridge by arranging several chambers in the biochemical reaction cartridge containing a DNA microarray and moving a solution through differential pressure.

In general, a DNA microarray is installed in a biochemical reaction cartridge with the microarray bonded and fixed. The biochemical reaction cartridge is assembled in a clean room for preventing contamination. The biochemical reaction cartridge is composed of two plates with irregularities and the DNA microarray and has a hermetically sealed internal space.

It is necessary to accumulate reagents (solutions), for example, a first hemolytic agent containing EDTA destroying cell walls and a second hemolytic agent containing a protein denaturant such as a surfactant, in chambers in the biochemical reaction cartridge. These reagents may be accumulated in advance in a planned chamber site in one of the plates that form the biochemical reaction cartridge, followed by the assembly of the biochemical reaction cartridge; or otherwise, the reagents may be injected through an external syringe pump or vacuum pump into the biochemical reaction cartridge after the assembly of the biochemical reaction cartridge.

However, a surface facing the probe-forming surface of the DNA microarray installed in the biochemical reaction cartridge was always exposed to the outside air.

On the other hand, known methods of moving a solution in the interior of a biochemical reaction cartridge utilize gravity, capillary action and electrophoresis. In addition, there is disclosed a small micropump that can be placed in the interior of a biochemical reaction cartridge, including a micropump using a heating device (Japanese Patent No. 2832117), a micropump using a piezoelectric element (Japanese Patent Application Laid-Open No. 2000-274375) and a diaphragm pump (National Publication of International Patent Application No. H11-509094).

SUMMARY OF THE INVENTION

In the case of the above-described biochemical reaction cartridge, the surface facing the probe-forming surface of the DNA microarray may be contaminated with dust in the air or by the touching of an examiner's hand, because the surface facing the probe-forming surface of the DNA microarray is exposed to the outside air during the period of time from the installation of the DNA microarray in the biochemical reaction cartridge, through the placement of the biochemical reaction cartridge in a reader such as a scanner, to probe detection. When detection is performed from the backside of the DNA microarray, dust in the air and stains from human hands attached to the backside of the DNA microarray block light emission in that portion and therefore cause reduction in apparent strength of detection light. In this case, the problem is that accurate detection can not be performed because size of DNA is small.

Particularly a fluorescently detecting biochemical reaction cartridge presents, in addition to the above-described problem, a problem with the progression of deterioration of a fluorescent dye caused by the exposure of a DNA microarray portion to light, resulting in inaccurate probe detection.

An object of the present invention is to provide a biochemical treatment equipment system comprising a biochemical reaction cartridge, which can solve the problems.

The present invention relates to a biochemical reaction cartridge comprising at least a reaction chamber for performing detection reaction of a target substance and a reaction information fetching section for fetching information on the detection reaction, wherein the biochemical reaction cartridge is provided with a covering unit that allows the reaction information fetching section to be at least in an exposed state and in a covered state.

The present invention also relates to biochemical treatment equipment comprising a mounting unit for mounting a biochemical reaction cartridge thereon, a stage for biochemical treatment of a sample by use of the sample and a solution in the biochemical reaction cartridge, a stage for detection of the biochemically treated sample by use of the biochemical reaction cartridge, and a moving unit for moving the biochemical reaction cartridge mounted on the mounting unit to the stage for biochemical treatment and the stage for detection, wherein the biochemical treatment equipment further comprises an unlocking unit for unlocking a shielding unit that shields, from the outside, a detection reaction information fetching section of the biochemical reaction cartridge moved to the stage for detection.

Moreover, the present invention relates to a biochemical treatment equipment system comprising: a biochemical reaction cartridge comprising at least a reaction chamber for performing detection reaction of a target substance, a detection reaction information fetching section for fetching information on the detection reaction which is exposed to the outside, a shielding unit for shielding the detection reaction information fetching section from the outside, and an inlet for injecting a sample therethrough;
biochemical treatment equipment comprising a mounting unit for mounting the biochemical reaction cartridge thereon, a stage for biochemical treatment of a sample by use of the sample and a solution in the biochemical reaction cartridge, a stage for detection of the biochemically treated sample by use of the biochemical reaction cartridge, and a moving unit for moving the biochemical reaction cartridge mounted on the mounting unit to the stage for biochemical treatment and the stage for detection; and a unit for injecting the sample into the biochemical reaction cartridge through the inlet of the biochemical reaction cartridge,
wherein the biochemical treatment equipment further comprises an unlocking unit for unlocking the shielding unit of the biochemical reaction cartridge mounted on the mounting unit.

The present invention has significantly reduced or completely eliminated the possibility that an examiner unintentionally touches a site of a biochemical reaction cartridge required for probe detection or other sites functionally required for the cartridge during the handling of the cartridge and the possibility of exposing these sites to the air. Moreover, the present invention has almost or completely eliminated the contamination of the sites with stains from hands, dirt in the air, and so on.

In addition, particularly for a fluorescently detecting biochemical reaction cartridge, the present invention has been capable of preventing the progression of deterioration of a fluorescent dye caused by the exposure of a DNA microarray portion to light.

As a result, the present invention has allowed accurate probe detection. Regarding a cartridge, if any, having the possibility of reducing the reliability of probe detection for the reason that a shutter is opened once, an operator can recognize that the cartridge is unavailable; or otherwise, the cartridge can be forced to be in a state of being unavailable. This has allowed the prevention of measurement with the cartridge before it starts.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 4 is a block diagram of a treatment equipment that controls the movement of a solution and various reactions in the biochemical reaction cartridge;
FIG. 5 is a flow chart of treatment procedures.

DETAILED DESCRIPTION OF THE PREFERRED EMBODIMENTS

Figure 1:
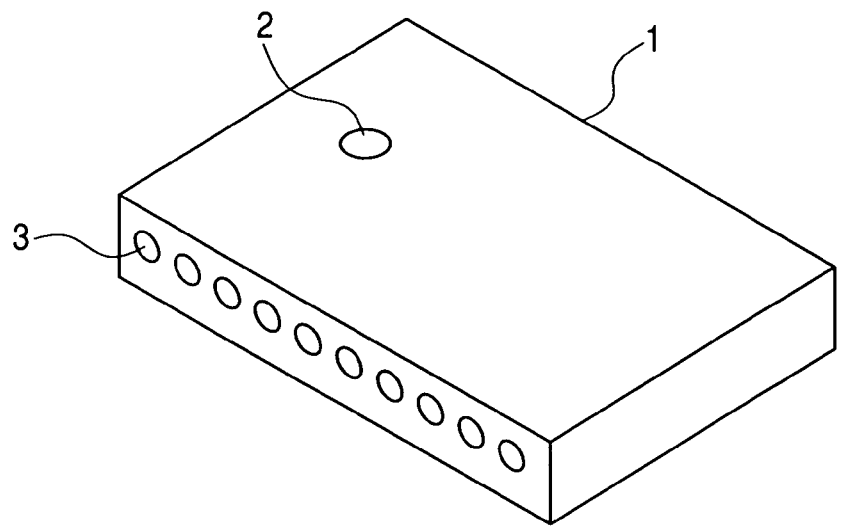
FIG. 1 is a perspective view of a biochemical reaction cartridge.

Preferred embodiments of the present invention will now be described in detail in accordance with the accompanying drawings.

The present invention comprises, when detection is performed using a biochemical reaction cartridge where a detection section is exposed to the outside: installing the detection section exposed to the outside into the biochemical reaction cartridge; hermetically sealing the interior of the biochemical reaction cartridge; and then providing a cover that prevents the detection section from coming into contact with the outside at least until just before the mounting of the biochemical reaction cartridge on biochemical treatment equipment or until just before detection with the biochemical treatment equipment or a detector.

In the biochemical reaction cartridge used in the present invention, sample-treating reagents (solutions) and/or chamber-washing reagents (solutions) and so on are accumulated in a chamber in the biochemical reaction cartridge. After being injected, a sample is treated with the reagents and so on and then detected in a detection reaction information fetching section, for example, a DNA microarray, for fetching information on whether or not the detection reaction is performed. In many cases, these examinations are performed using a treatment equipment that performs steps to probe detection, after the movement of the solution and various reactions in the biochemical reaction cartridge are controlled. However, in some biochemical treatment equipment, a portion where biochemical reaction takes place is different from a detection section.

Such a biochemical reaction cartridge is affected by the outside, when the detection reaction information fetching section is exposed to the outside. Therefore, after the installation of the DNA microarray into the biochemical reaction cartridge, it is preferred that the detection section such as the DNA microarray and/or an electrical contact should be shielded from the outside at least until just before the mounting (placement) of the biochemical reaction cartridge on the treatment equipment.

On the other hand, when the above-described biochemical reaction is allowed to occur, heat is sometimes supplied from the outside. In this case, the removal of a shield is more preferable in terms of constant and uniform temperatures. Therefore, it is preferred that the shield should be allowed to be removed. A place for bringing about biochemical reaction and a place for performing detection are located in different positions in the biochemical treatment equipment. However, when biochemical reaction and detection are performed in one biochemical treatment equipment, the shield is released at the time of biochemical reaction and then kept released until detection, without problems. Meanwhile, when different biochemical treatment equipment are used in biochemical reaction and detection, it is preferred that the detection section should be covered again with the shield that have been removed for bringing about biochemical reaction.

The shielding of the detection reaction information fetching section from the outside can be achieved by covering, for example with a seal or a shutter, the detection reaction information fetching section exposed to the outside. In the case of a fluorescently detecting biochemical reaction cartridge, it is preferred that the seal or the shutter should be composed of a material that dose not pass light therethrough.

Moreover, it is preferred that the reaction cartridge should be provided with an indicator that can check whether the reaction information fetching section is in an exposed state or in a covered state. The indicator may have, for example, a shape of a cartridge accompanying the movement of the shutter or may be provided in a seal unit.

Preferably, the biochemical treatment equipment is constructed to detect the exposed state of the reaction information fetching section of the cartridge based on the indicator, by use of an indicator-reading unit provided in the biochemical treatment equipment.

The indicator-reading unit, which is appropriately available according to an indicator used, includes conventional reading sensors such as CCD, CMOS and bar-code sensors.

Alternatively, the indicator-reading unit may be, for example, a method of electrically detecting the open/close state of the shutter.

In case that the shutter is used as a shield from the outside, when the shutter that covers the detection reaction information fetching section is moved to expose the detection reaction information fetching section to the outside, it is preferred to provide a mechanism for preventing error measurement for discontinuing the use of the biochemical reaction cartridge. The biochemical reaction cartridge is provided with, as this mechanism for preventing error measurement, a stopper that prevents the shutter from recovering the initial state when the shutter that covers the detection reaction information fetching section is moved to expose the detection section to the outside. The discontinuation of the use of the biochemical reaction cartridge can be achieved by:

(1) putting, in sight or out of sight, a mark that indicates that the shutter is opened, in a state in which the shutter is returned to the position of the stopper;
(2) blocking an inlet for injecting a sample therethrough, in a state in which the shutter is returned to the position of the stopper;
(3) using the stopper to prevent the mounting (placement) of the biochemical reaction cartridge on the treatment equipment that performs probe detection; and
(4) moving the shutter placed once by, for example, a knocking unit placed in an examination stage of the treatment equipment.

When the biochemical reaction cartridge of the present invention is used to perform examination, it is preferred that the treatment equipment (biochemical treatment equipment) should comprise a mounting unit for mounting the biochemical reaction cartridge thereon; a stage for biochemical treatment of a sample by use of the sample and a solution in the biochemical reaction cartridge; a stage for detection of the biochemically treated sample by use of the biochemical reaction cartridge; and a moving unit for moving the biochemical reaction cartridge mounted on the mounting unit to the stage for biochemical treatment and the stage for detection, wherein the biochemical treatment equipment further comprises an unlocking unit for unlocking a shielding unit that shields, from the outside, a detection reaction information fetching section of the biochemical reaction cartridge moved to the stage for detection.

A detection method of a sample of the present invention comprises the steps of: injecting the sample into a biochemical reaction cartridge where at least a reagent (solution) for treating the sample is accumulated in a chamber and a detection reaction information fetching section is shielded from the outside by a shielding unit; mounting the biochemical reaction cartridge on biochemical treatment equipment; subjecting the sample to hybridization; and fetching information on detection reaction from the sample, wherein the detection method further comprises the step of unlocking the shielding unit to expose a detection section to the outside, which is performed immediately before the step of mounting the biochemical reaction cartridge on biochemical treatment equipment or during or after the movement of the biochemical reaction cartridge to an examination stage of the biochemical treatment equipment.

In addition, the present invention relates to a biochemical treatment equipment system comprising: a biochemical reaction cartridge comprising at least one chemical reaction chamber that accommodates a solution for biochemically treating a sample, a reaction chamber for performing detection reaction of a target substance in the biochemically treated sample, a detection reaction information fetching section for fetching information on whether or not the detection reaction is performed that is exposed to the outside, a shielding unit for shielding the detection reaction information fetching section from the outside, and an inlet for injecting the sample therethrough; biochemical treatment equipment comprising a mounting unit for mounting the biochemical reaction cartridge thereon, a stage for biochemical treatment of the sample by use of the sample and the solution in the biochemical reaction cartridge, a stage for detecting information on reaction of the biochemically treated sample from the detection reaction information fetching section by use of the biochemical reaction cartridge, and a moving unit for moving the biochemical reaction cartridge mounted on the mounting unit to the stage for biochemical treatment and the stage for detecting information on reaction of the biochemically treated sample from the detection reaction information fetching section; and a unit for injecting the sample into the biochemical reaction cartridge through the inlet of the biochemical reaction cartridge, wherein the biochemical treatment equipment further comprises an unlocking unit for unlocking a shielding unit of the biochemical reaction cartridge mounted on the mounting unit.

Furthermore, the detection method of the present invention further comprises the steps of: installing a detection section exposed to the outside into the biochemical reaction cartridge and hermetically sealing the interior of the biochemical reaction cartridge; and then providing the biochemical reaction cartridge with a cover that prevents the detection section from coming into contact with the outside at least until just before detection or until just before the placement of the biochemical reaction cartridge in a detector.

EXAMPLES

Example 1

Example 1 of the present invention will be described in detail with reference to drawings.

FIG. 1 is a perspective view of a biochemical reaction cartridge 1 contained in a biochemical treatment equipment system.

A sample inlet 2 for injecting a sample such as blood by use of a syringe or the like is provided on the upper portion of the biochemical reaction cartridge 1 and sealed with a rubber cap. Several nozzle inlets 3 that apply or reduce pressure by inserting nozzles therein for moving an internal solution are provided on the side of the cartridge 1. A rubber cap is fixed in each of the nozzle inlets 3. The other side of the cartridge 1 has the same structure.

These rubber caps are provided for preventing the entry of the air into the biochemical reaction cartridge 1.

The body of the biochemical reaction cartridge 1 is composed of a transparent or semitransparent synthetic resin such as polymethyl methacrylate (PMMA), an acrylonitrile-butadiene-styrene (ABS) copolymer, polystyrene, polycarbonate, polyester and polyvinyl chloride. When reactants in the cartridge 1 do not require optical reaction, the body does not have to be composed of a transparent material.

Figure 2:
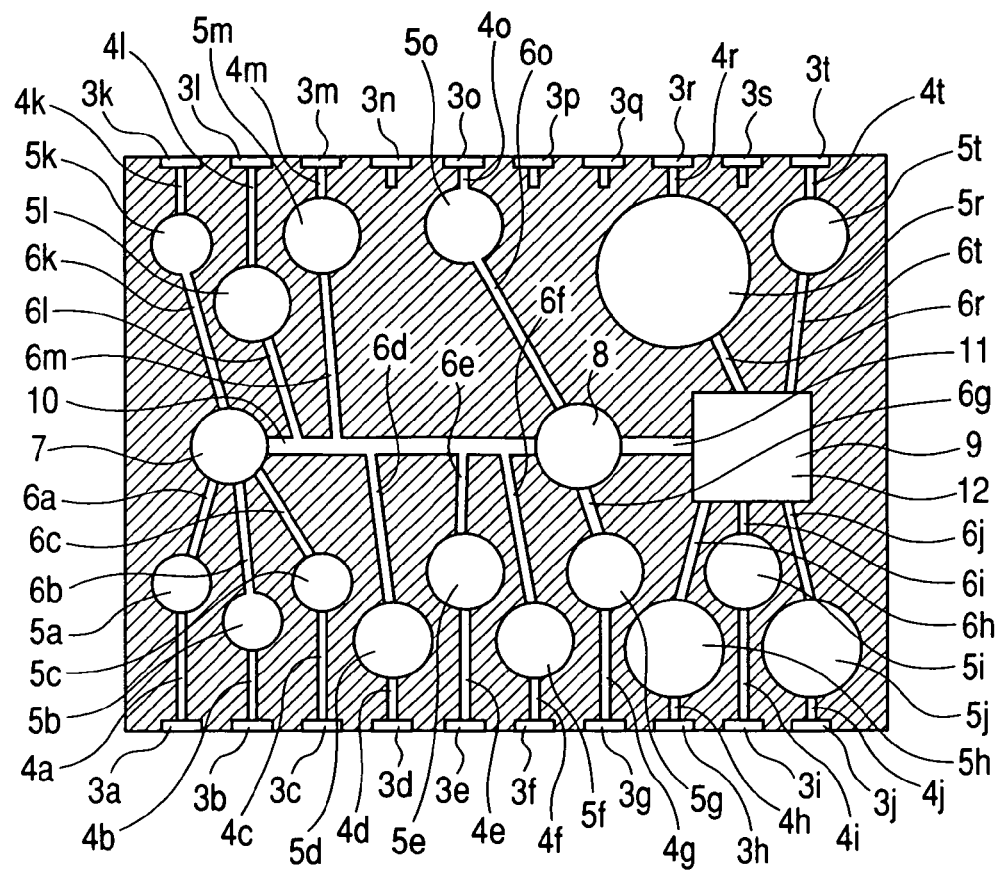
FIG. 2 is a plan sectional view of the biochemical reaction cartridge.

FIG. 2 shows a plan sectional view of the biochemical reaction cartridge 1. Ten nozzle inlets $3a$ to $3j$ are provided on one side of the biochemical reaction cartridge 1, and ten nozzle inlets $3k$ to $3t$ are also provided on the other side of the biochemical reaction cartridge 1. The nozzle inlets $3a$ to $3t$ are respectively communicated via corresponding air passages $4a$ to $4t$ each passing the air therethrough with a chamber 5, a place for storing a solution or bringing about reaction.

In FIG. 2, the nozzle inlets $3n$, $3p$, $3q$ and $3s$ are not communicated with the chamber 5 and are kept in reserve, because they are not used. Namely, the nozzle inlets $3a$ to $3j$ are respectively communicated via the passages $4a$ to $4j$ with chambers $5a$ to $5j$. The nozzle inlets $3k$, $3l$, $3m$, $3o$, $3r$ and $3t$ on the other side are respectively communicated via the passages $4k$, $4l$, $4m$, $4o$, $4r$ and $4t$ with chambers $5k$, $5l$, $5m$, $5o$, $5r$ and $5t$.

The sample inlet 2 is communicated with a chamber 7. The chambers $5a$, $5b$, $5c$ and $5k$ are communicated with the chamber 7. The chambers $5g$ and $5o$ are communicated with a chamber 8. The chambers $5h$, $5i$, $5j$, $5r$ and $5t$ are communicated with a chamber 9. In addition, the chamber 7 is communicated with via a passage 10 with the chamber 8 that is communicated via a passage 11 with the chamber 9. The passage 10 is communicated with the chambers $5d$, $5e$, $5f$, $5l$ and $5m$ via corresponding passages $6d$, $6e$, $6f$, $6l$ and $6m$, respectively.

A square hole is made in the underside of the chamber 9. A DNA microarray 12 where dozens to hundreds of thousands of different types of DNA probes are arranged with high-density on the surface of a solid phase such as a glass plate having a size on the order of a square inch is affixed to the square hole with its probe-forming surface facing upward.

This DNA microarray 12 can be used to examine a large number of genes at a time by performing hybridization with sample DNA. These DNA probes are regularly arranged in matrix form. Therefore, information on each of the DNA probes can be pulled with ease by bringing it into correspondence with each location address (position indicated by column and row numbers) of the DNA probes arranged on the DNA microarray 12.

Genes to be examined include infectious viruses, bacteria and disease-associated genes. In addition, for example, polymorphism of each individual becomes a subject of examination.

Figure 3A:
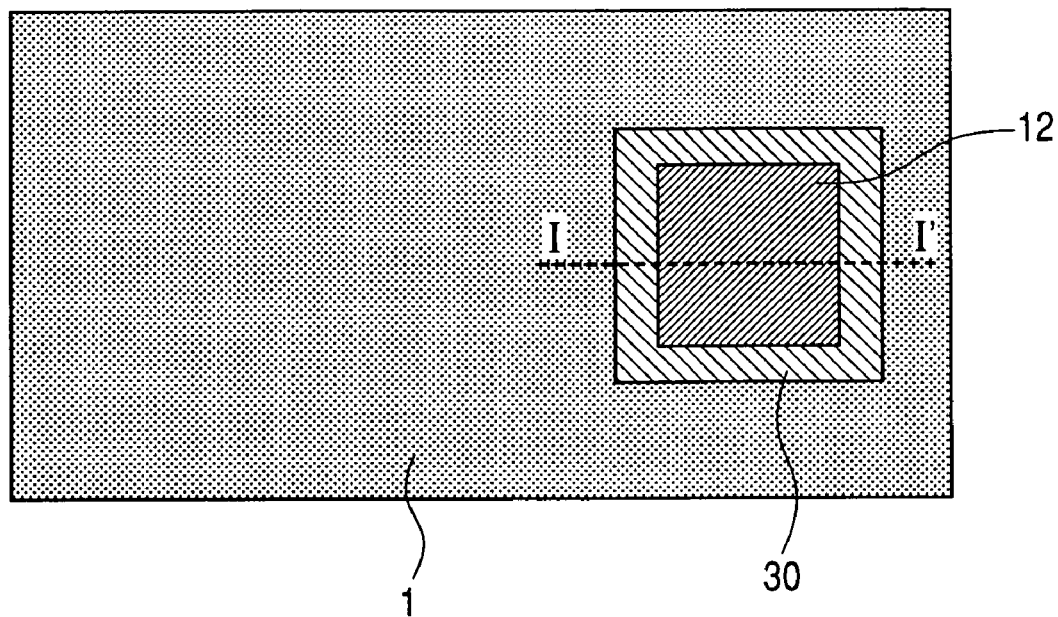
FIGS. 3A and 3B are diagrams where a seal is affixed to the biochemical reaction cartridge.
Figure 3B:
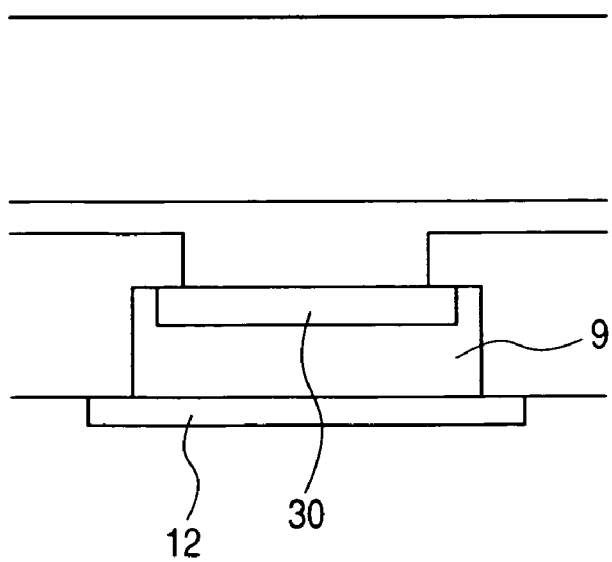

FIG. 3A is a diagram showing the biochemical reaction cartridge 1 from the underside thereof. FIG. 3B is a sectional view of a portion of the biochemical reaction cartridge 1 where the DNA microarray 12 is arranged. The DNA microarray 12 is affixed to the chamber 9 so as to cover an opening of the square hole of the chamber 9 in the biochemical reaction cartridge 1. A seal 30 affixed so as to cover the opening of the square hole of the chamber 9 in the biochemical reaction cartridge 1 is affixed to the opening at least after the installment of the DNA microarray 12 in the biochemical reaction cartridge 1. Then, the seal 30 is removed when measurement is performed.

The backside of the DNA microarray 12 can be protected against dust in the air and stains such as the sebum of examiners by covering, with the seal 30, the opening of the square hole of the chamber 9 in the biochemical reaction cartridge 1.

A probe detection section 33 described below (see FIG. 4) performs probe detection by scanning the DNA microarray 12 from the backside thereof. Therefore, it is preferred that an examiner should remove the seal 30 immediately before placing the biochemical reaction cartridge 1 in a treatment equipment described below.

A first hemolytic agent containing EDTA destroying cell walls and a second hemolytic agent containing a protein denaturant such as a surfactant are accumulated in the chambers $5a$ and $5b$, respectively. Silica-coated particles of a magnetic material that adsorb DNA thereon are accumulated in the chamber $5c$. First and second extraction detergents used for DNA purification in DNA extraction are accumulated in the chambers $5l$ and $5m$.

The chamber $5d$ is filled with an eluent consisting of a buffer with a low salt concentration that elutes DNA from the particles of the magnetic material, and the chamber $5g$ is filled with a mixture solution of primers, polymerase, a dNTP solution, a buffer, Cy3-dUTP containing a fluorescent material and so on, which are necessary for PCR. A detergent containing a surfactant for washing fluorescently labeled sample DNA that is unhybridized and the fluorescent label is accumulated in the chambers $5h$ and $5j$. Alcohol for drying the interior of the chamber 9 including the DNA microarray 12 is accumulated in the chamber $5i$.

The chamber $5e$ is a chamber for collecting dust of blood other than DNA. The chamber $5f$ is a chamber for collecting the waste liquids of the first and second extraction detergents from the chambers $5l$ and $5m$. The chamber $5r$ is a chamber for collecting the waste liquids of the first and second extraction detergents. The chambers 5k, 5o and 5t are blank chambers provided for preventing solutions from flowing into the nozzle inlet.

A sample in a liquid state such as blood is injected into this biochemical reaction cartridge 1, which is in turn placed in the treatment equipment described below. Then, the extraction and amplification of DNA or the like are performed in the interior of the cartridge 1. Furthermore, hybridization between the amplified sample DNA and the DNA probes on the DNA microarray located in the interior of the cartridge 1 as well as the washing of the fluorescently labeled sample DNA that is unhybridized and the fluorescent label is performed, followed by probe detection by fluorescence measurement.

A sample may be injected into the biochemical reaction cartridge 1 after the cartridge 1 is placed in the treatment equipment.

FIG. 4 shows a diagrammatic view of the treatment equipment that controls the movement of a solution and various reactions in the biochemical reaction cartridge 1 and performs steps to probe detection.

A carriage 31, in which the biochemical reaction cartridge 1 is placed, is capable of moving along carriage rails 32 at least between two positions of a table 13 and a probe detection section 33 described below and is driven by a drive motor (not shown). An electromagnet 14 activated during the extraction of DNA or the like from a sample in the cartridge 1 and a Peltier device 15 for controlling a temperature during the amplification of DNA from the sample by a method such as PCR (Polymerase Chain Reaction) are placed on the table 13. There is also provided a Peltier device 16 that controls the temperature of the biochemical reaction cartridge 1 from above.

The Peltier device 16 controls a temperature when the amplified sample DNA hybridizes with the DNA probes on the DNA microarray located in the interior of the cartridge 1 and when the unhybridized sample DNA is washed.

The operation of a variety of equipment integrated in the treatment equipment is controlled through a controller 17 by a program prestored in the treatment equipment.

Both sides of the table 13 are provided with electrically driven syringe pumps 18 and 19 and pump blocks 22 and 23 provided with ten pump nozzles 20 and ten pump nozzles 21, respectively on one side thereof, which are entrances for discharging or aspirating the air through these pumps 18 and 19. Several electrically driven selector valves (not shown) are placed between the electrically driven syringe pumps 18 and 19 and the pump nozzles 20 and 21 and connected together with the pumps 18 and 19 to the controller 17. The controller 17 is connected to an input portion 24 where an examiner performs input. The controller 17 can control the pump nozzles by controlling the opening/closing of the electrically driven selector valves connected to the ten pump nozzles 20 and to the ten pump nozzles 21.

In the present Example, an examiner allows a syringe to penetrate the rubber cap of the sample inlet 2 and injects blood used as a sample, which then flows into the chamber 7. The examiner then places, the biochemical reaction cartridge 1 in the carriage 31. When at least a treatment start signal is sent from the input portion 24 of the treatment equipment to the treatment equipment, the carriage 31 is moved to the position of the table 13. The pump blocks 22 and 23 are moved in the directions of the arrows in FIG. 4 by the drive motor (not shown). Thereby, the pump nozzles 20 and 21 are inserted through the rubber caps into nozzles inlets 3 on both sides of the cartridge 1.

Since the nozzle inlets 3a to 3t exist all on two surfaces, that is, on both sides of the biochemical reaction cartridge 1, the shapes and layouts of the electrically driven syringe pumps 18 and 19, the electrically driven selector valve, the pump blocks 22 and 23 incorporating the pump nozzles therein, and so on can be simplified. In addition, the pump nozzles 20 and 21 can be inserted only by simple operation, that is, by simultaneously sandwiching the cartridge 1 between the pump blocks 22 and 23, while the necessary chamber 5 and passages are secured. This can simplify the structures of the pump blocks 22 and 23. Furthermore, all of the nozzle inlets 3a to 3t are placed to have the same height, that is, placed to be in straight line form. As a result, all of the passages 4a to 4t connected to the nozzle inlets 3a to 3t have the same height. This simplifies the fabrication of the passages 4a to 4t.

The probe detection section 33 is composed of a well known detector such as a scanner. The carriage 31 is moved so that the DNA microarray 12 in the biochemical reaction cartridge 1 is positioned right above a reading lens of the probe detection section 33. Then, probe detection is performed.

When an examiner inputs a treatment start command at the input portion 24, treatment begins. The controller 17 allows the carriage 31 to be moved and positioned right above the table 13 and also allows the pump blocks 22 and 23 to be moved in the directions of the arrows shown in FIG. 4.

Next, treatment procedures with the treatment equipment that uses the biochemical reaction cartridge 1 where blood used as a sample is accumulated in the chamber 7 will be described in detail with reference to a flow chart shown in FIG. 5.

The seal 30 is removed from the opening of the square hole of the chamber 9 in the biochemical reaction cartridge 1 to expose the DNA microarray 12. Then, the biochemical reaction cartridge 1 is placed in the carriage 31 of the biochemical treatment equipment.

When the carriage 31 is moved to the position of the table 13, the pump blocks 22 and 23 are moved in the directions of the arrows shown in FIG. 4 by the drive motor (not shown). Thereby, the pump nozzles 20 and 21 are inserted through the rubber caps into the nozzles inlets 3 on both sides of the cartridge 1.

<Step S1 (Pouring and Stirring of First Hemolytic Agent)>

The controller 17 opens only the nozzle inlets 3a and 3k. The air is discharged from the electrically driven syringe pump 18 and aspirated from the pump 19 to pour the first hemolytic agent of the chamber 5a into the chamber 7 containing blood. In this case, depending on the viscosity of the hemolytic agent and the resistance of the passage, the aspiration of the air from the pump 19 is controlled to start after 10 to 200 msec of the initiation of the discharge of the air from the pump 18. As a result, the solution flows smoothly without jumping out of the passage at the front position of the flowing solution.

By such pressurization and pressure reduction controlled by staggering timings of the supply and aspiration of the air, the solution can be poured smoothly. It is possible to pour the solution more smoothly by performing detailed control in such a way that the aspiration of the air from the electrically driven syringe pump 19 is linearly increased from the initiation of the discharge of the air from the pump 18. The same holds true for the movement of solutions described below.

The control of the supply of the air can be achieved easily by using the electrically driven syringe pumps 18 and 19. Only the nozzle inlets 3a and 3o are opened. The discharge and aspiration of the air by the pumps 18 and 19 are alternately repeated. Operation that pours the solution of the chamber 7 into the passage 10 and subsequently returns the solution is repeated to perform stirring. Alternatively, stirring may be performed with bubbles occurring by continuously discharging the air from the pump 19.

Figure 6:
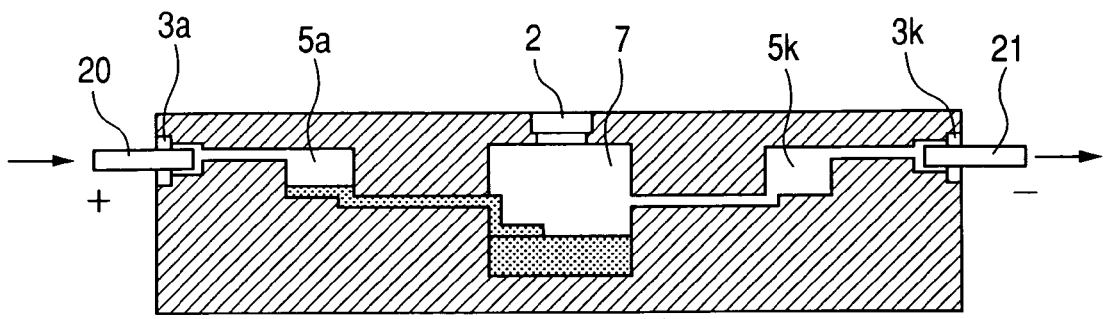
FIG. 6 is a vertical sectional view of some chambers.

FIG. 6 is a sectional view taken along the chambers 5a, 7 and 5k shown in FIG. 2 and shows a state in which pressure is applied by inserting the pump nozzle 20 into the nozzle inlet 3a and reduced by inserting the pump nozzle 21 into the nozzle inlet 3k to pour the first hemolytic agent of the chamber 5a into the chamber 7 containing blood.

<Step S2 (Pouring and Stirring of Second Hemolytic Agent) to Step S3 (Pouring and Stirring of Particles of Magnetic Material)>

Next, at Step S2, only the nozzle inlets 3b and 3k are opened to pour the second hemolytic agent of the chamber 5b into the chamber 7 in the same way as above. At Step S3, only the nozzle inlets 3c and 3k are opened to pour the particles of the magnetic material of the chamber 5c into the chamber 7 in the same way as above. At both Steps S2 and S3, stirring is performed in the same way as Step S1. At Step S3, DNA obtained from the dissolution of a cell at Steps S1 and S2 is attached to the particles of the magnetic material.

<Step S4 (Activation of Electromagnet and Capture of Particles of Magnetic Material and DNA)>

Next, the electromagnet 14 is turned on, and only the nozzle inlets 3e and 3k are opened. The air is discharged from the electrically driven syringe pump 19 and aspirated from the pump 18 to move the solution of the chamber 7 to the chamber 5e. During this movement of the solution, the particles of the magnetic material and the DNA are captured on the electromagnet 14 of the passage 10. The aspiration and discharge of the air by the pumps 18 and 19 are alternately repeated to put the solution into two reciprocating motions between the chambers 7 and 5e, thereby improving DNA capture efficiency. Although additional reciprocating motions can further enhance capture efficiency, extra treatment time is required.

Since the particles of the magnetic material, as described above, are used to capture DNA with the DNA running on a small passage of approximately 1 to 2 mm in width and approximately 0.2 to 1 mm in height, DNA can be captured with high efficiency. The same holds true for RNA and proteins used as a target substance to be captured.

<Step S5 (Washing with First Extraction Detergent and Capture)>

Next, the electromagnet 14 is turned off, and only the nozzle inlets 3f and 3l are opened. The air is discharged from the electrically driven syringe pump 19 and aspirated from the pump 18 to move the first extraction detergent of the chamber 5l to the chamber 5f. In this case, the particles of the magnetic material and the DNA captured at Step S4 are moved together with the extraction detergent, followed by washing. After two reciprocating motions as in Step S4, the electromagnet 14 is turned on to put the solution into additional two reciprocating motions in the same way as above. As a result, the particles of the magnetic material and the DNA are collected onto the electromagnet 14 of the passage 10. The solution is then returned to the chamber 5l.

<Step S6 (Washing with Second Extraction Detergent and Capture)>

Subsequently, the nozzle inlets 3f and 3m are used to perform additional washing with the second extraction detergent of the chamber 5m in the same procedures as Step S5.

<Step S7 (Separation of Particles of Magnetic Material and DNA by Pouring Eluent)>

Next, only the nozzle inlets 3d and 3o are opened with the electromagnet 14 turned on. The air is discharged from the electrically driven syringe pump 18 and aspirated from the pump 19 to thereby move the eluent of the chamber 5d to the chamber 8.

During this procedure, the particles of the magnetic material and the DNA are separated by the action of the eluent. Only the DNA is then moved together with the eluent to the chamber 8, while the particles of the magnetic material remain in the passage 10. In this way, DNA extraction and purification are performed. Because a chamber containing an extraction detergent and a chamber for colleting waste liquids after washing are prepared, it is possible to perform DNA extraction and purification in the biochemical reaction cartridge 1.

<Step S8 (Pouring of Reagents for PCR and PCR by Controlling Peltier Device)>

Next, only the nozzle inlets 3g and 3o are opened. The air is discharged from the electrically driven syringe pump 18 and aspirated from the pump 19 to pour the reagent for PCR of the chamber 5g into the chamber 8. Besides, only the nozzle inlets 3g and 3t are opened. The discharge and aspiration of the air by the pumps 18 and 19 are alternately repeated. Operation that pours the solution of the chamber 8 into the passage 11 and subsequently returns the solution is repeated to perform stirring. After the Peltier device 15 is controlled to maintain the solution in the chamber 8 at a temperature of 96° C. for 10 minutes, the eluted DNA is amplified by 30 PCR cycles of 96° C. for 10 sec, 55° C. for 10 sec and 72° C. for 1 min.

<Step S9 (Hybridization by Controlling Peltier Device and Stirring)>

Next, only the nozzle inlets 3g and 3t are opened. The air is discharged from the electrically driven syringe pump 18 and aspirated from the pump 19 to move the solution of the chamber 8 to the chamber 9. In addition, the Peltier device 16 is controlled to perform hybridization with the solution in the chamber 9 maintained at 45° C. for 2 hours. During this procedure, the discharge and aspiration of the air by the pumps 18 and 19 are alternately repeated. While operation that pours the solution of the chamber 9 into the passage 6t and subsequently returns the solution is repeated to perform stirring, hybridization is promoted.

<Step S10 (Washing with First Detergent)>

Next, only the nozzle inlets 3h and 3r are opened with the solution maintained at 45° C. The air is discharged from the electrically driven syringe pump 18 and aspirated from the pump 19 to move the solution in the chamber 9 to the chamber 5r, while the first detergent of the chamber 5h is poured through the chamber 9 into the chamber 5r. The aspiration and discharge of the air by the pumps 18 and 19 are alternately repeated to put the solution into two reciprocating motions between the chambers 5h and 5r via the chamber 9. Finally, the solution is returned to the chamber 5h. In this way, the fluorescently labeled sample DNA that is unhybridized and the fluorescent label are washed.

Figure 7:
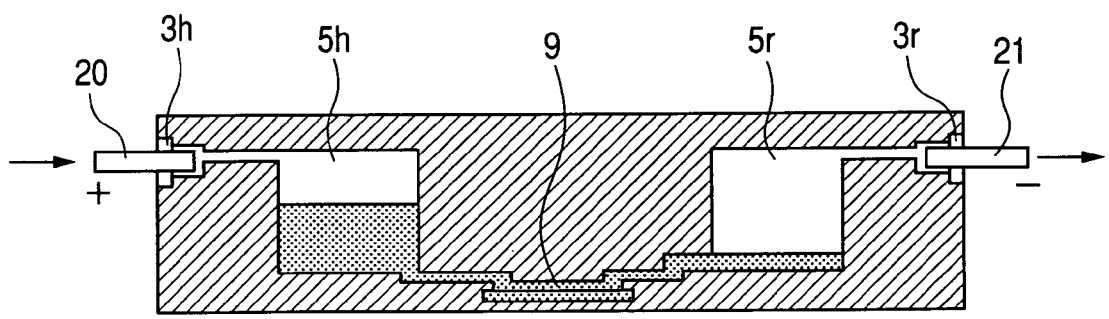
FIG. 7 is a vertical sectional view of other chambers.

FIG. 7 is a sectional view taken along the chambers 5h, 9 and 5r shown in FIG. 2 and shows a state in which pressure is applied by inserting the pump nozzle 20 into the nozzle inlet 3h and reduced by inserting the pump nozzle 21 into the nozzle inlet 3r to pour the first detergent of the chamber 5h through the chamber 9 into the chamber 5r.

<Step S11 (Washing with Second Detergent)>

While the solution is maintained at 45° C., the nozzle inlets 3j and 3r are used to perform washing with the second detergent of the chamber 5j by undergoing the same steps as Step S10. Finally, the solution is returned to the chamber 5j. Because the chambers 5h and 5j each containing the detergent and the chamber 5r for colleting waste liquids after washing are prepared as described above, it is possible to wash the DNA microarray 12 in the biochemical reaction cartridge 1.

<Step S12 (Movement of Alcohol and Drying)>

At the final step, only the nozzle inlets 3i and 3r are opened. The air is discharged from the electrically driven syringe pump 18 and aspirated from the pump 19 to move the alcohol of the chamber 5i through the chamber 9 to the chamber 5r. Then, only the nozzle inlets 3i and 3t are opened. The air is discharged from the pump 18 and aspirated from the pump 19 to dry the interior of the chamber 9.

Subsequently, the pump blocks 22 and 23 are moved in the direction away from the biochemical reaction 1 by the controller 17, followed by the removal of the pump nozzles 20 and 21 from the nozzle inlet 3 of the cartridge 1. Next, the carriage 31 is moved to the probe detection section 33. In the present Example, probe detection is performed by fluorescence measurement.

In the present Example, the opening of the biochemical reaction cartridge 1 is usually kept closed to the outside after the integration of the DNA microarray 12 into the biochemical reaction cartridge 1 and is opened at the time of detection.

Figure 8:
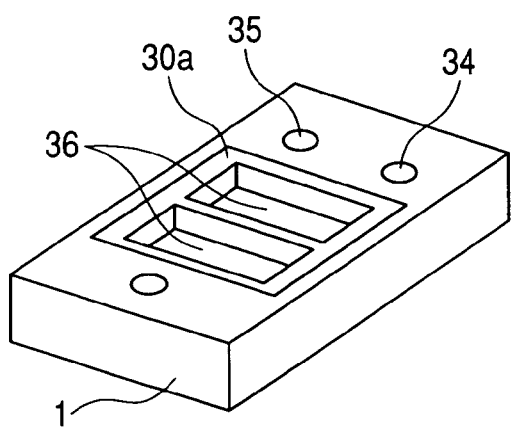
FIG. 8 is a diagram (front side) where a seal is affixed to a biochemical reaction cartridge that uses a current-detecting DNA chip.
Figure 9:
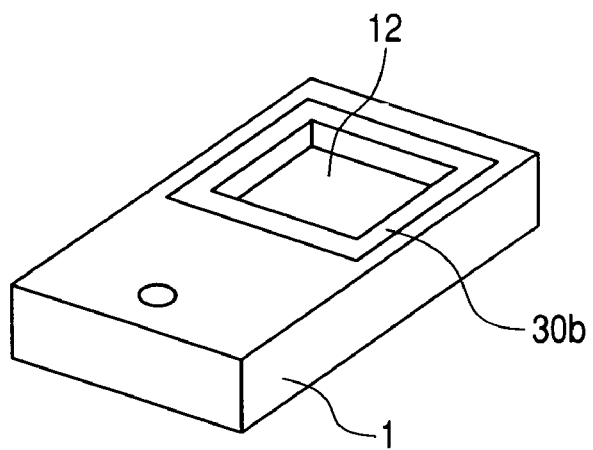
FIG. 9 is a diagram (backside) where the seal is affixed to the biochemical reaction cartridge that uses the current-detecting DNA chip.

Next, an example of a biochemical reaction cartridge that uses a current-detecting DNA chip will be described with reference to drawings. FIGS. 8 and 9 are block diagrams showing the whole biochemical reaction cartridge that uses the current-detecting DNA chip from the front side and the back side, respectively.

An inlet 34 for supplying a hybridization solution, a detergent, or the like into the DNA chip and an outlet 35 for discharging these solutions are provided on the front side of the biochemical reaction cartridge 1 shown in FIG. 8. After the biochemical reaction cartridge 1 is loaded into the body of equipment (not shown), the inlet 34 and the outlet 35 are constructed to form a joint with a liquid-handling portion located in the body of the equipment. In order to immobilize DNA probes on an electrode 36, contamination with dust in the air and stains such as sebum must be prevented for avoiding the denaturation and inactivation of the DNA probes. Accordingly, a seal 30a prevents the electrode 36 from exposure to the air. The contact electrode 36 for detection is constructed to be exposed by removing the seal 30a, and to come into contact with an electrode located in the body of the equipment after the biochemical reaction cartridge 1 is loaded into the body of the equipment.

The backside of the biochemical reaction cartridge 1 shown in FIG. 9 is hollowed out to create, in a rectangle shape, a portion that corresponds to a heater element when the biochemical reaction cartridge 1 is loaded into the body of the equipment. For example, when a DNA microarray 12 is composed of a material that passes light therethrough, the deterioration of the probes due to light is not desirable. Therefore, a seal 30b is affixed to this portion. The DNA microarray 12 is constructed to expose its backside by removing the seal 30b.

The DNA microarray 12 is provided with metal electrodes (not shown), for example, gold electrodes. The DNA probes are affixed to each of the electrodes by a spotting method.

When a material that does not pass light therethrough is used in the seal 30b and a shutter described below, it is preferred to color a transparent material. Coloring with a block color or the like is preferred for intercepting light form the outside. Although it is necessary to take a thickness into consideration in addition to a color, the degree of interception of light varies depending on, for example, the storage space and period of the biochemical reaction cartridge. However, it is obvious that a method generally used for intercepting light can be adopted, though a particular detailed description is omitted.

The principle of detection is based on a scheme for detecting the value of a current, wherein a hybridization solution is mixed with an intercalating agent (intercalator), and electrons travel through the DNA probes from the intercalating agent (intercalator) attached to hybridized target DNA. Detection is performed by applying voltage to the DNA probes with them dipped in the solution.

As described above, the present invention can be applied not only to the surroundings of a site involved in detection with the biochemical reaction cartridge constructed to perform probe detection by fluorescence measurement, but also to a site involved in detection with the cartridge constructed to electrically perform probe detection.

Moreover, the present invention may be applied not only to a site involved in the detection of hybridized substances, but also to a site involved in other chemical reactions such as antigen-antibody reaction.

Furthermore, the present invention may be applied not only to a site involved in detection, but also to the surroundings of a site functionally required for the biochemical reaction cartridge.

As described above, the present invention has significantly reduced the possibility that an examiner unintentionally touches a site of a biochemical reaction cartridge involved in probe detection or other sites functionally required for the cartridge during the handling of the cartridge and the possibility of exposing these sites to the air. Moreover, the present invention has almost eliminated the contamination of the sites with stains from hands, dirt in the air, and so on. In addition, particularly for a fluorescently detecting biochemical reaction cartridge, the present invention has been capable of preventing the progression of deterioration of a fluorescent dye caused by the exposure of a DNA microarray portion to light. In summary, the present invention has allowed the accurate detection of target DNA in a sample with probes.

In the present Example and subsequent Examples, the DNA microarray is bonded and fixed in advance in the biochemical reaction cartridge. However, for preventing the deterioration of reagent solutions such as hemolytic agents due to their storage, the solutions can also be injected into the chambers of the biochemical reaction cartridge on a stage 31 immediately before examination. Similarly, the DNA microarray can be loaded into the biochemical reaction cartridge immediately before examination. In this case, packing for hermetic sealing is formed in the opening of the square hole of the chamber 9 in the biochemical reaction cartridge, in which the DNA microarray is loaded. The packing can be achieved by hermetically sealing the opening after the DNA microarray is loaded therein.

Example 2

Example 2 of the present invention will be described in detail with reference to drawings.

Figure 10:
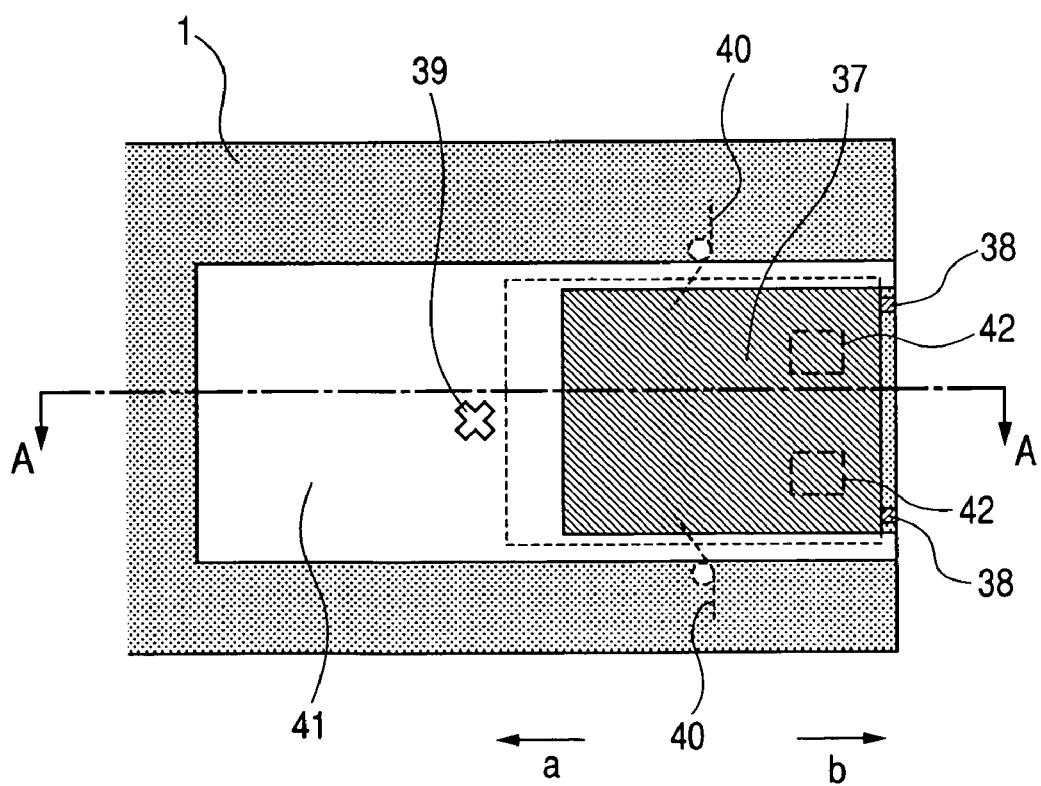
FIG. 10 is a diagram showing the underside of a biochemical reaction cartridge according to Example 2.
Figure 11:
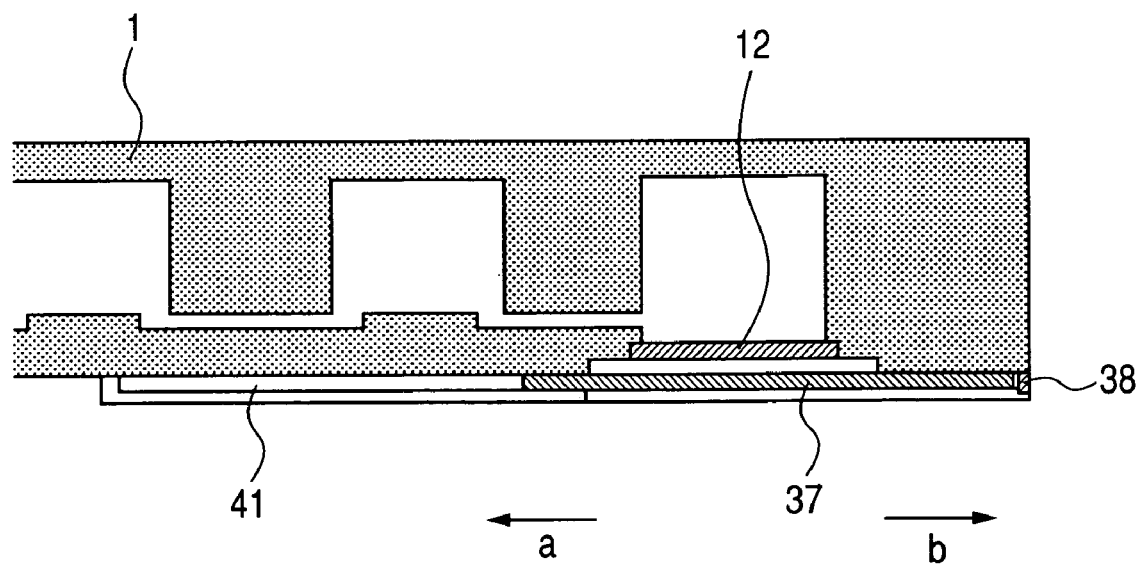
FIG. 11 is a sectional view of the biochemical reaction cartridge according to Example 2.
Figure 12:
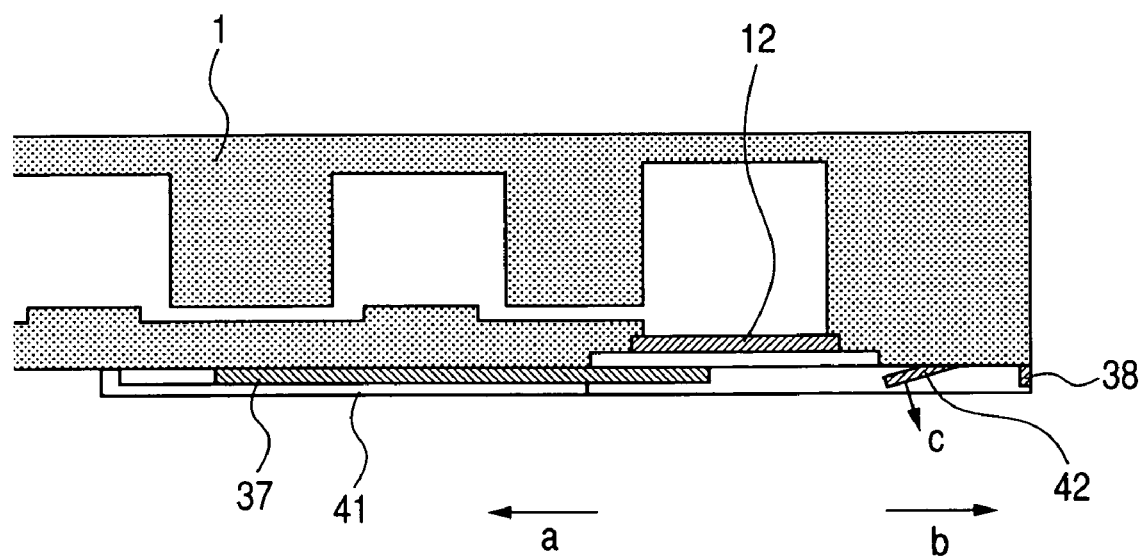
FIG. 12 is a sectional view of the biochemical reaction cartridge according to Example 2.

FIG. 10 is a diagram showing an unused biochemical reaction cartridge 1 from the underside thereof, in which a shutter that covers an opening has no history indicating that the shutter is opened, once covering the opening. FIG. 11 is a sectional view taken along the A-A line in FIG. 10, in which a shutter 37 can be slid in the direction of the arrow a in FIG. 10. FIG. 12 shows a state in which the shutter 37 is moved in the direction of the arrow a and a stopper 42 is protruded in the direction of the arrow c.

In the present Example, the shutter 37 is used instead of the seal 30 to cover the opening. The shutter 37 that covers the opening is constructed in a stopper 38, an availability/unavailability display window 39, a torsion coil spring 40, a shutter cover 41 and the stopper 42.

The backside of a DNA microarray 12 is exposed by sliding the shutter 37 in the direction of the arrow a. The shutter 37 is powered in the direction of the arrow b by the torsion coil spring 40. The stopper 38 is a stopper for restricting the movement of the shutter 37 in the direction of the arrow b.

The shutter cover 41 functions as a movement guide for the shutter 37 and is constructed to be capable of accommodating the shutter 37 when the shutter 37 is opened. The availability/unavailability display window 39 is provided in a site visible to an examiner. The availability/unavailability display window 39 is placed in a position that goes out of sight when the shutter 37 is slid beyond a fixed distance in the direction of the arrow a in FIG. 10.

As shown in FIG. 12, the shutter 37 is pulled in the direction of the arrow a so that a DNA microarray 12 can be placed. After the DNA microarray 12 is installed in the biochemical reaction cartridge, the opening is immediately closed by pressing the stopper 42 in the direction opposite to the direction of the arrow c and then pressing the shutter 37 until the shutter 37 strikes the stopper 38. It is preferred that the shutter 42 should be kept closed until just before the detection of target DNA in a sample with probes. Immediately before the detection of target DNA in a sample with probes, the shutter 37 is slid in the direction of the arrow a to thereby expose the backside of the DNA microarray 12.

The shutter 37 prevents decrease in the accuracy of the detection of target DNA in a sample with probes at a subsequent step, which is caused by an examiner's unintentional touch on the DNA microarray 12 and the attachment of dust in the air to the DNA microarray 12.

FIG. 12 illustrates a state in which after the DNA microarray is placed in the biochemical reaction cartridge and the shutter 37 is closed, the shutter 37 is moved by applying external forces to the shutter 37 in the direction of the arrow a in FIG. 12. The stopper 42 with spring properties, which is formed integrally with or separately from the box of the biochemical reaction cartridge 1, acts to prevent the return of the shutter 37 in the following way: the stopper 42 is originally charged in the direction opposite to the direction of the arrow c and then released in the direction of the arrow c simultaneously with the movement of the shutter 37 beyond a fixed distance in the direction of the arrow a and away from the stopper 42.

It is preferred that the stopper 42 should be positioned so that the stopper 42 is opened when the shutter 37 is moved to a position where the backside of the DNA microarray 12 is exposed to the air.

When the shutter 37, as shown in FIG. 12, is moved to the position where the backside of the DNA microarray 12 is exposed to the air, dust in the air may be attached to the DNA microarray 12 or an examiner may touch the DNA microarray 12. This sometimes results in a hindrance to the accurate detection of target DNA in a sample with probes. Once the shutter 37 is moved to the position where the backside of the DNA microarray 12 is exposed to the air, it is not preferred to use this biochemical reaction cartridge.

Figure 13:
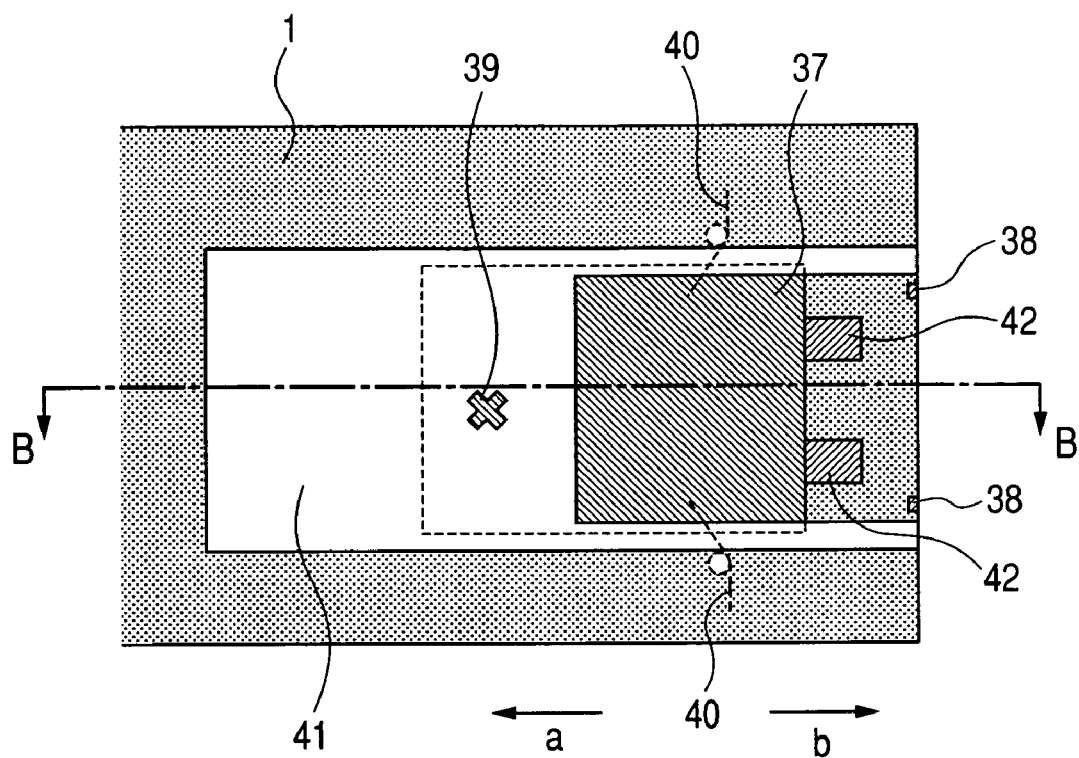
FIG. 13 is a diagram showing the biochemical reaction cartridge according to Example 2.
Figure 14:
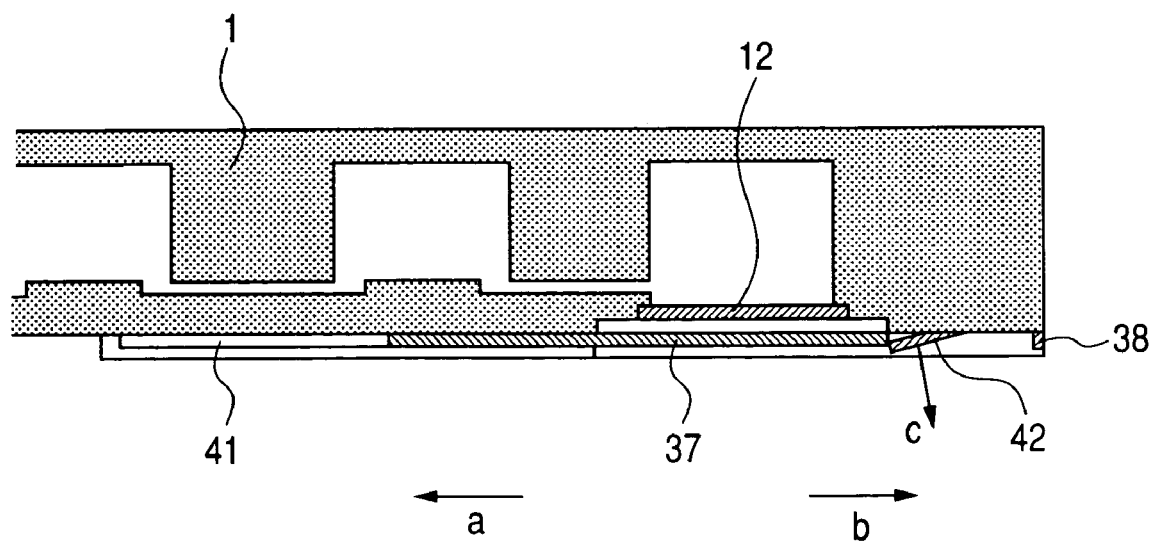
FIG. 14 is a sectional view of the biochemical reaction cartridge according to Example 2.

FIG. 13 is a bottom view of the biochemical reaction cartridge 1 showing the state of the shutter 37 with the stopper 42 released. FIG. 14 shows a sectional view taken along the B-B line in FIG. 13.

When released, the stopper 42 is protruded onto the path over which the shutter 37 is moved. Therefore, the shutter 37 can not be returned to the original position. The shutter 37 can be returned merely to the position of the stopper 42 and, in this state, is formed in a position where the availability/unavailability display window 39 is not visible.

For this reason, the biochemical reaction cartridge 1 in which the availability/unavailability display window 39 is not visible indicates that the biochemical reaction cartridge 1 is unavailable. Because the shutter 37 is never opened in the biochemical reaction cartridge 1 in which the availability/unavailability display window 39 is visible, the DNA microarray 12 is guaranteed not to expose its backside to the air until just before the detection of target DNA in a sample with probes.

The shutter 37 of the biochemical reaction cartridge 1 having this structure is opened by a knocking unit (not shown) that is provided in the body of the equipment when the biochemical reaction cartridge 1 is moved to a probe detection section 33.

Because the shutter 37 is opened when the biochemical reaction cartridge 1 is moved to the probe detection section 33, the DNA microarray 12 is never exposed to the air until just before the detection of target DNA in a sample with probes. That is, the DNA microarray 12 is kept very clean until just before the detection of target DNA in a sample with probes.

In the foregoing, the availability/unavailability display window 39 is constructed to go out of sight when the shutter is moved to a position where the probe detection section 33 is exposed to the air. However, it is obvious that the availability/unavailability display window 39 can be rendered visible when the shutter is moved to a position where the probe detection section 33 is exposed to the air.

When biochemical reaction and detection are performed in different biochemical treatment equipment as described above, it is necessary to cover the detection section again with the shutter that has been released at the time of biochemical reaction. In this case, though not shown, a mechanism such as a pushing bar for pushing the stopper 42 upward is provided in a position that faces the stopper 42 of the biochemical treatment equipment. When the detection section 12 is covered with the shutter 37, the stopper 42 is pushed upward with this pushing bar. Then, the shutter 37 is moved to the original position, thereby allowing the covering of the detection section. The detection section is exposed to the outside in this case and however, is not contaminated, because a room in which the biochemical treatment equipment is located is placed under dust control. In addition, because the shutter is moved without manual operation, human contamination is not attached to the detection section.

As described above, the present invention has significantly reduced the possibility that an examiner unintentionally touches a site of a biochemical reaction cartridge required for the detection of target DNA in a sample with probes or other sites functionally required for the cartridge during the handling of the cartridge and the possibility of exposing these sites to the air. Moreover, the present invention has almost eliminated the contamination of the sites with stains from hands, dirt in the air, and so on. In addition, particularly for a fluorescently detecting biochemical reaction cartridge, the present invention has been capable of preventing the progression of deterioration of a fluorescent dye caused by the exposure of a DNA microarray portion to light. In summary, the present invention has allowed the accurate detection of target DNA in a sample with probes. Regarding a cartridge, if any, having the possibility of reducing the reliability of the detection of target DNA in a sample with probes for the reason that the shutter is opened once, an operator can recognize that the cartridge is unavailable. This has allowed the prevention of measurement with the cartridge before it starts.

Example 3

Example 3 of the present invention will be described in detail with reference to drawings.

Figure 15:
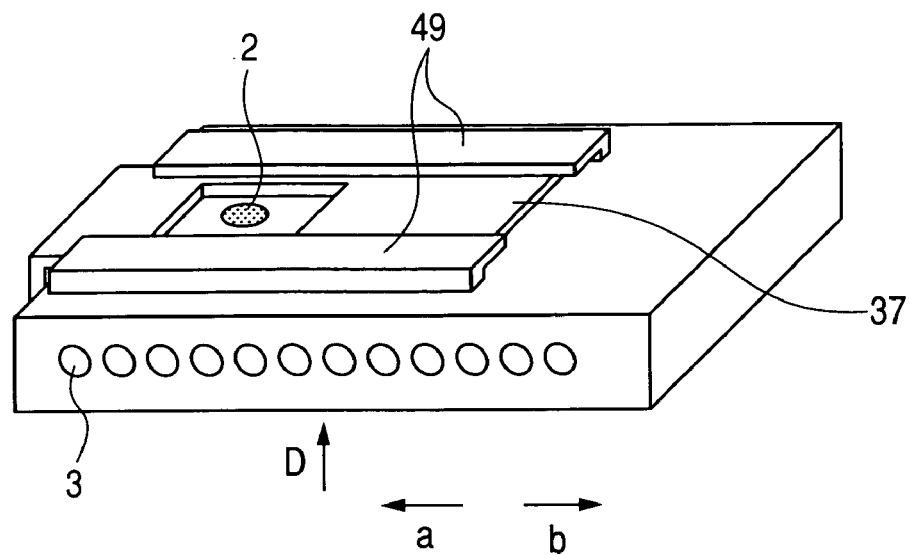
FIG. 15 is a diagram showing a biochemical reaction cartridge according to Example 3.
Figure 16:
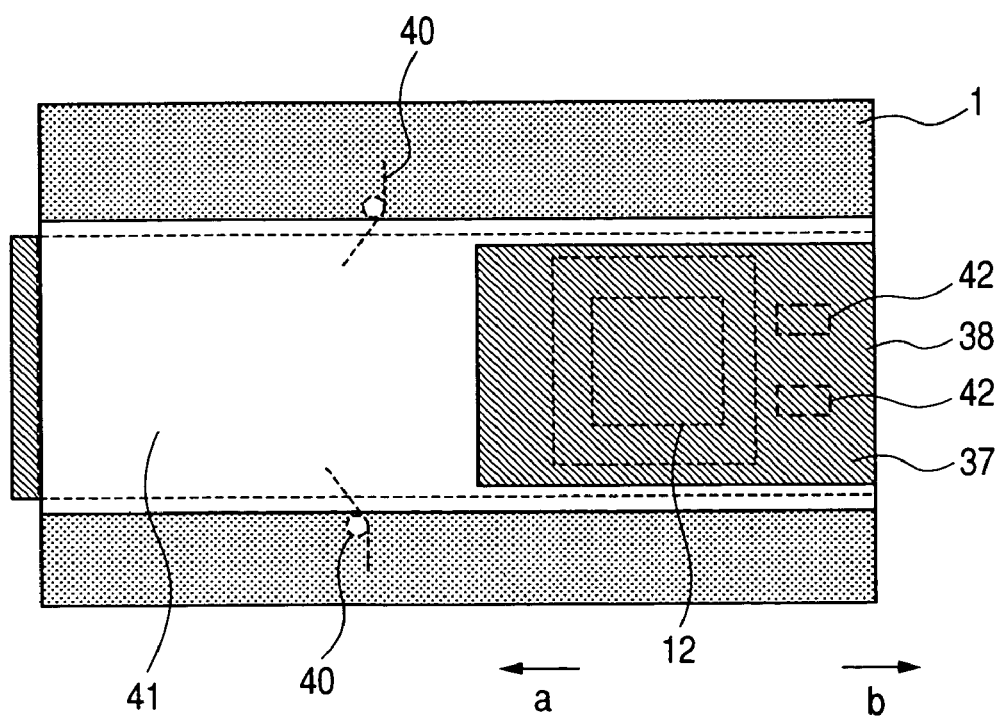
FIG. 16 is a diagram showing the underside of the biochemical reaction cartridge according to Example 3.

FIG. 15 is a perspective view of the whole biochemical reaction cartridge 1. FIG. 16 is a diagram showing the backside of the biochemical reaction cartridge from the arrow D in FIG. 15. A shutter 37 has a C-shape capable of being slid in the directions of the arrows a and b in FIG. 16. In such a structure, a sample inlet 2 and an opening on the backside of a DNA microarray 12 are constructed so that one of them is opened with the other closed.

Although detailed description is omitted, the DNA microarray is placed in the biochemical reaction cartridge with the shutter 37 opened, followed by the closing of the shutter 37, as in Example 2.

FIGS. 15 and 16 illustrate a state in which the sample inlet 2 is opened and the opening on the backside of the DNA microarray 12 is closed, that is, the unused state of the biochemical reaction cartridge.

In the present Example, the followings are different from the above Example 2: the absence of a stopper 38 and an availability/unavailability display window 39; the addition of a shutter cover 49; and a change in the shapes of the shutter 37 and a shutter cover 41.

Figure 17:
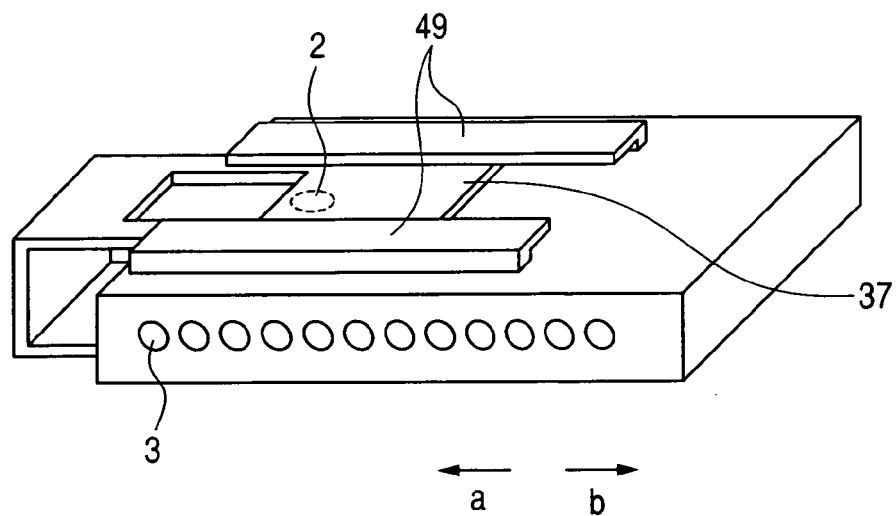
FIG. 17 is a diagram showing the biochemical reaction cartridge according to Example 3.
Figure 18:
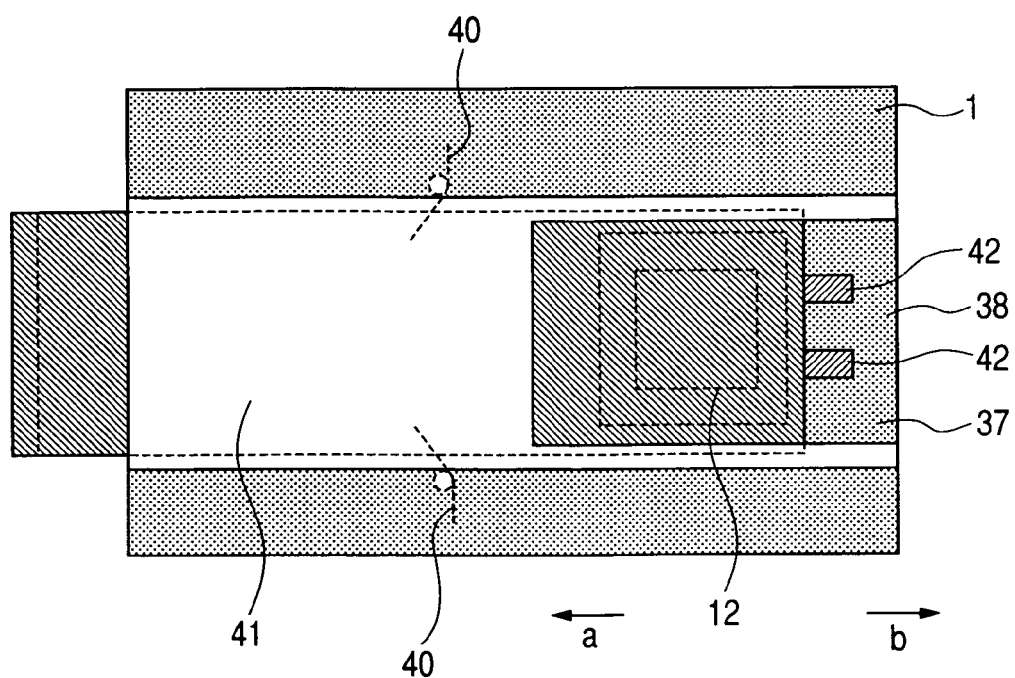
FIG. 18 is a diagram showing the underside of the biochemical reaction cartridge according to Example 3.

FIGS. 17 and 18 are, respectively, a diagram showing a state in which the shutter 37 is slid in the direction of the arrow a by a mistake and a portion of the opening on the backside of the DNA microarray is exposed to the outside air. When the shutter 37 is moved to a position where a portion of the opening on the backside of the DNA microarray is exposed to the out side air, a charged stopper 42 jumps. Thus, the shutter 37 is caught in the stopper 42 and is not returned to the original position. The shutter 37 is powered in the direction of the arrow b by a torsion coil spring 40. In this state, the sample inlet 2 is blocked by the shutter 37 as shown in FIG. 17.

In the biochemical reaction cartridge 1 manipulated by the above-described structure without opening the shutter 37 before being placed in the body of equipment, the shutter 37 is opened only by operation that moves a carriage 31 to a probe detection section 33 after the placement of the cartridge 1 in the body of the equipment and by a knocking unit (not shown) for the shutter 37 provided in the body of the equipment (not shown). As a result, the DNA microarray 12 is exposed to the air. That is, the DNA microarray 12 is kept very clean until just before the detection of target DNA in a sample with probes.

Figure 19:
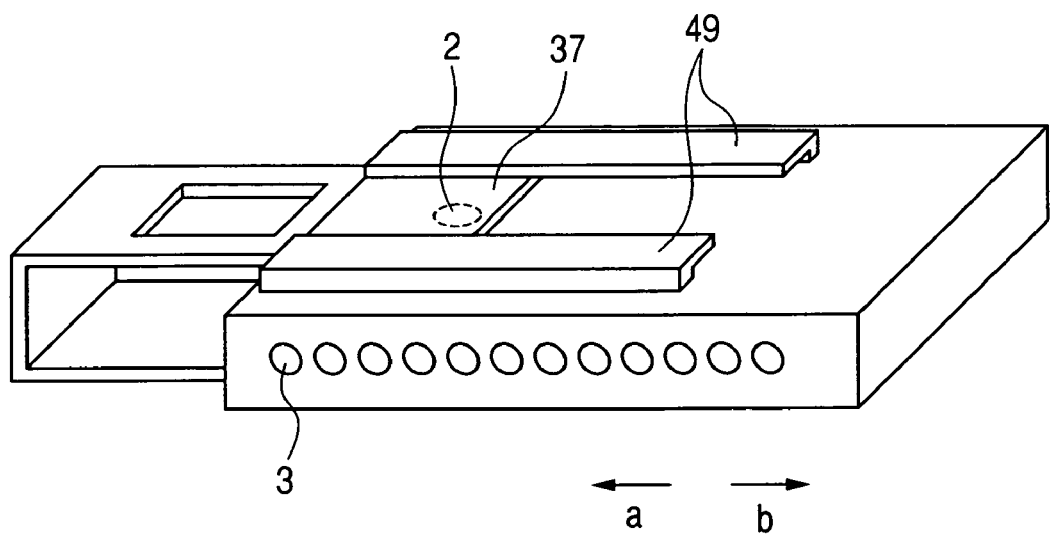
FIG. 19 is a diagram showing the biochemical reaction cartridge according to Example 3.
Figure 20:
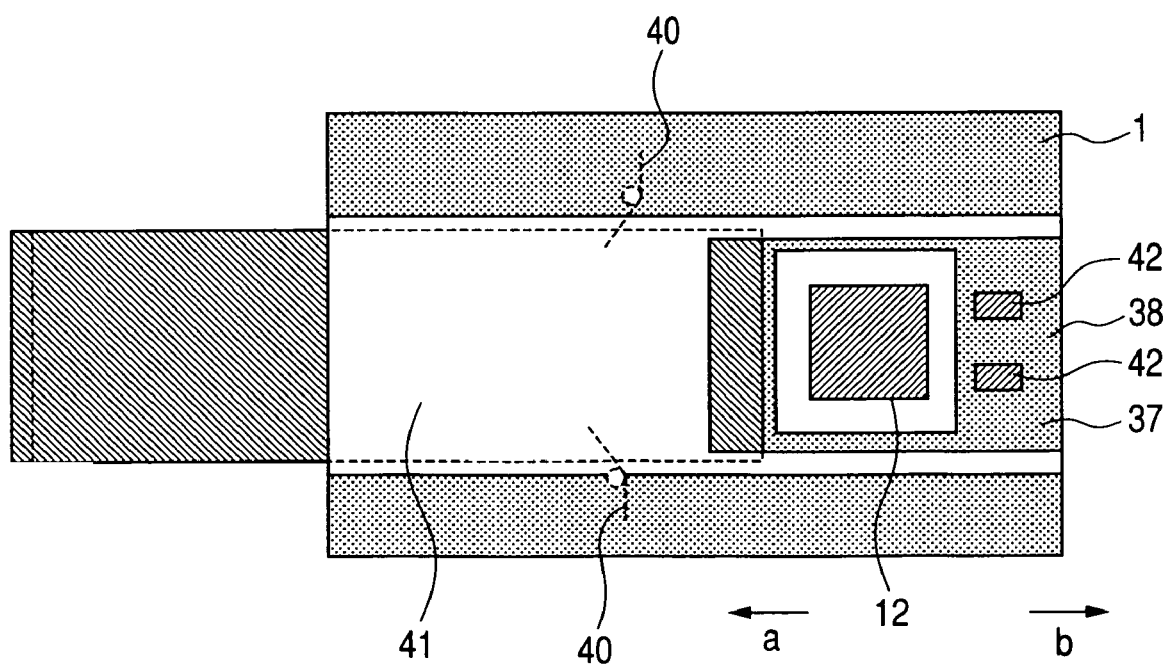
FIG. 20 is a diagram showing the underside of the biochemical reaction cartridge according to Example 3.

FIGS. 19 and 20 are, respectively a diagram showing the biochemical reaction cartridge 1 at the time of detection of target DNA in a sample with probes. The knocking unit (not shown) provided in the body of the equipment and the carriage 31 are operated to thereby open the shutter 37. The DNA microarray 12 is exposed to the outside air only after this procedure.

It is obvious that the shutter 37 can be opened by striking the shutter 37 with the knocking unit after the carriage 31 is moved to the detection section.

As described above, the present invention has significantly reduced the possibility that an examiner unintentionally touches a site of a biochemical reaction cartridge required for the detection of target DNA in a sample with probes or other sites functionally required for the cartridge during the handling of the cartridge and the possibility of exposing these sites to the air. Moreover, the present invention has almost eliminated the contamination of the sites with stains from hands, dirt in the air, and so on. In addition, particularly for a fluorescently detecting biochemical reaction cartridge, the present invention has been capable of preventing the progression of deterioration of a fluorescent dye caused by the exposure of a DNA microarray portion to light. In summary, the present invention has allowed the accurate detection of target DNA in a sample with probes. Regarding a cartridge, if any, having the possibility of reducing the reliability of the detection of target DNA in a sample with probes for the reason that the shutter is opened once, the cartridge can be forced to be in a state of being unavailable by blocking the sample inlet 2 with the shutter 37. This has allowed the prevention of measurement with the cartridge before it starts.

Example 4

Example 4 will be described in detail with reference to drawings.

Figure 21:
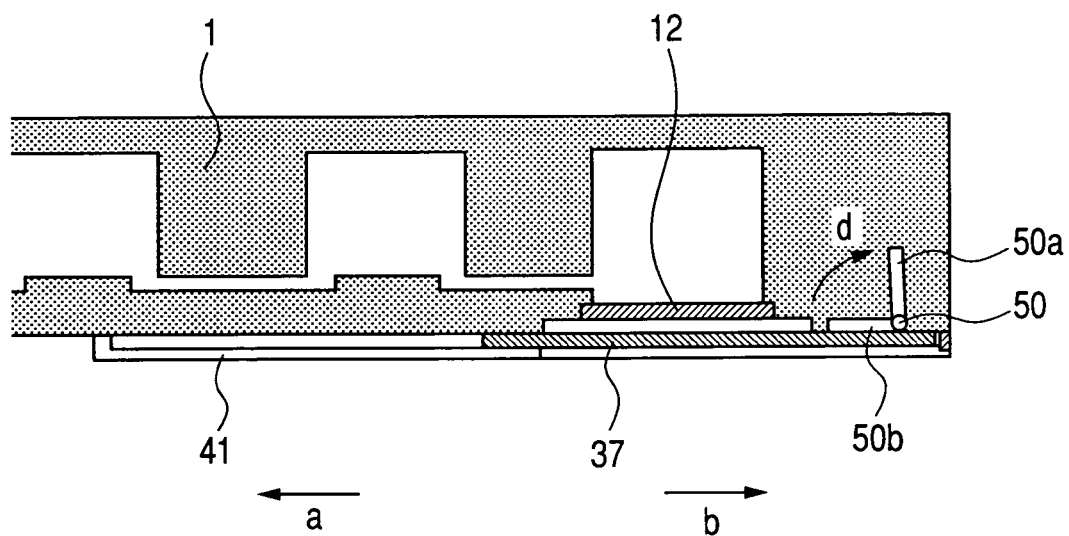
FIG. 21 is a sectional view of a biochemical reaction cartridge according to Example 4.

FIG. 21 is a diagram showing a portion of the cross section of a cartridge 1 according to the present Example.

A spring hinge 50 has one end 50a immobilized within the cartridge 1 and the other end 50b charged in the direction of the arrow d in FIG. 21 by a shutter 37.

The present Example is different from Example 2 in that the cartridge 1 lacks an availability/unavailability display window 39 and a stopper 42 and the spring hinge 50 is added.

Although detailed description is omitted, a DNA microarray in the present Example is also placed in the biochemical reaction cartridge with the shutter 37 opened, as in Example 2, followed by the closing of the shutter 37 after the spring hinge 50 is pushed downward to a position that allows the movement of the shutter 37.

Figure 22:
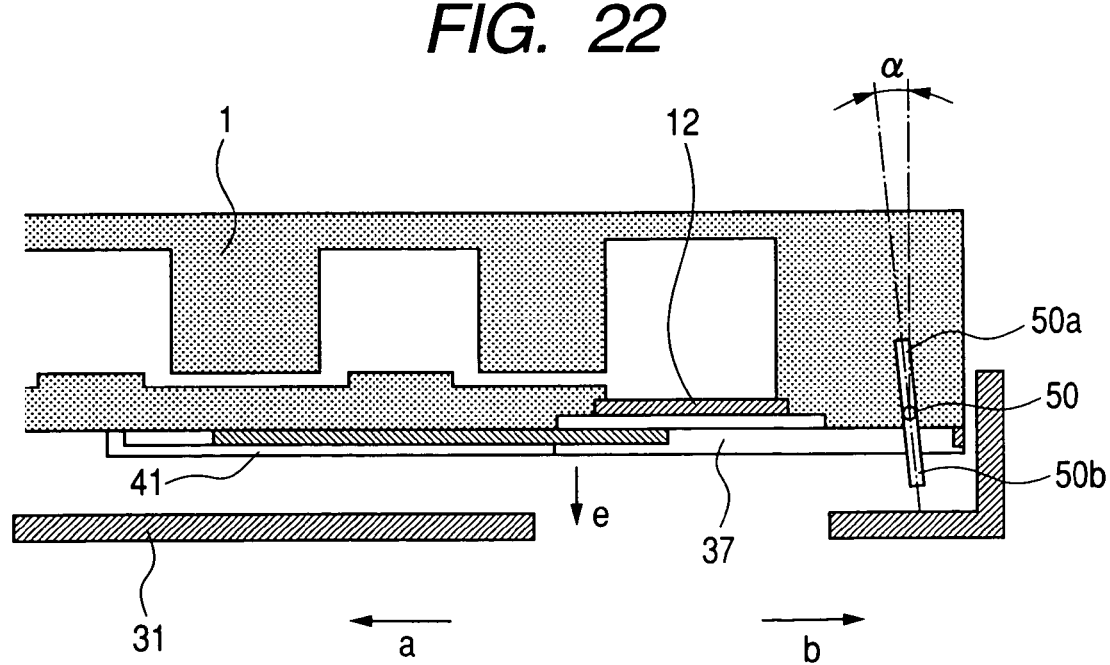
FIG. 22 is a sectional view of the biochemical reaction cartridge according to Example 4.

When the shutter 37 is improperly slid in the direction of the arrow a to expose a portion of an opening on the backside of the DNA microarray 12 to the outside air, the charged end 50b of the spring hinge jumps opposite to the direction of the arrow d. Therefore, the spring hinge 50 becomes a hindrance to the placement of the biochemical reaction cartridge 1 in a carriage 31. As a result, the biochemical reaction cartridge 1 can not be placed in the carriage 31 (see FIG. 22).

Legs of the spring hinge 50 are opened at an angle of 180 degrees in a natural state. In this case, the direction of installation (direction shown by the arrow e in FIG. 22) for the installation of the spring hinge 50 and the biochemical reaction cartridge 1 with respect to the carriage 31 forms a certain angle ($\alpha$ degree in FIG. 22). Thereby, there is no chance that the spring hinge 50 is charged again by external forces from the carriage 31. As a result, the biochemical reaction cartridge 1 is never placed in the carriage 31.

In the above-described structure, only the biochemical reaction cartridge 1 without a history indicating that the shutter 37 is opened before the placement of the carriage in the body of equipment can be placed in the carriage 31. The shutter 37 of the biochemical reaction cartridge 1 is opened by a knocking unit (not shown) provided in the body of the equipment (not shown), when the carriage 31 is placed in the body of the equipment and then moved to a probe detection section 33. The DNA microarray 12 is never exposed to the air until the shutter 37 is opened. For this reason, the DNA microarray 12 is kept very clean until just before the detection of target DNA in a sample with probes.

As described above, the present invention has significantly reduced the possibility that an examiner unintentionally touches a site of a biochemical reaction cartridge required for the detection of target DNA in a sample with probes or other sites functionally required for the cartridge during the handling of the cartridge and the possibility of exposing these sites to the air. Moreover, the present invention has almost eliminated the contamination of the sites with stains from hands, dirt in the air, and so on. In addition, particularly for a fluorescently detecting biochemical reaction cartridge, the present invention has been capable of preventing the progression of deterioration of a fluorescent dye caused by the exposure of a DNA microarray portion to light. In summary, the present invention has allowed the accurate detection of target DNA in a sample with probes. Regarding a cartridge, if any, having the possibility of reducing the reliability of the detection of target DNA in a sample with probes for the reason that the shutter is opened once, the cartridge can be forced to be in a state of being unavailable by using the spring hinge so as not to permit the placement of the cartridge in the carriage. This has allowed the prevention of measurement with the cartridge before it starts.

Example 5

Example 5 of the present invention will be described in detail with reference to drawings.

Figure 23:
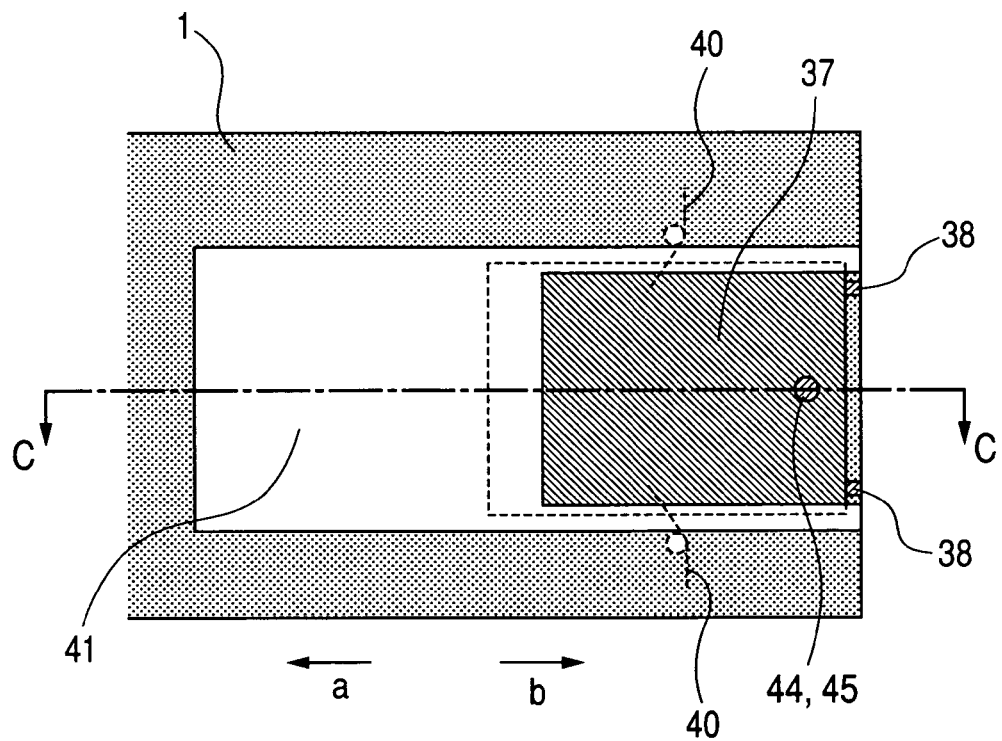
FIG. 23 is a diagram showing the underside of a biochemical reaction cartridge according to Example 5.
Figure 24:
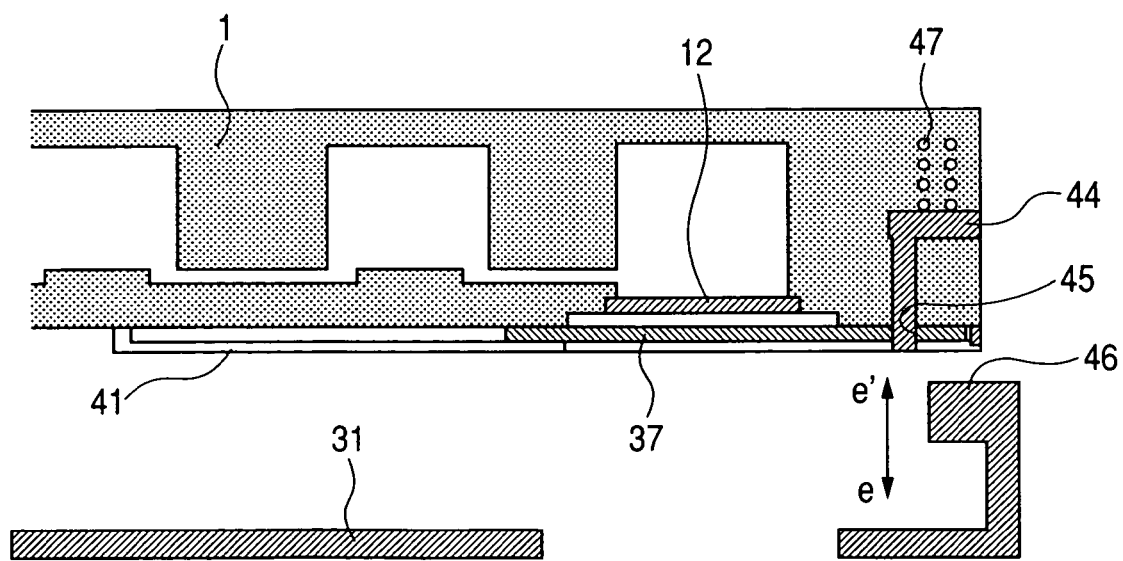
FIG. 24 is a diagram showing sections of the biochemical reaction cartridge and a carriage according to Example 5.

FIG. 23 is a diagram showing a biochemical reaction cartridge 1 from the underside thereof. FIG. 24 is a diagram showing the section of the biochemical reaction cartridge 1 and the section of a carriage 31, which are taken along the C-C line in FIG. 23, and illustrates a state of the biochemical cartridge 1 before its placement.

The present Example is different from Example 2 in that the cartridge lacks an availability/unavailability display window 39 and a stopper 42 and a lock pin 44, a lock hole 45, a lock lever 46 and a lock spring 47 are added.

The lock pin 44 can be moved in the directions of the arrows e and e' in FIG. 24 and is powered in the direction of the arrow e by the lock spring 47 that is a compression spring.

Although detailed description is omitted, it is obvious that a DNA microarray is placed in the biochemical reaction cartridge with a shutter 37 opened, followed by the closing of the shutter 37, as in Example 2.

In the above-described structure, the lock pin 44 is kept fitted with the lock hole 45 provided in the shutter 37 before the biochemical reaction cartridge 1 is placed in the carriage 31. The lock pin 44 is incorporated in the biochemical reaction cartridge 1 so as not to allow the examiner's manual operation of the lock pin 44. Therefore, the shutter 37 is never opened when the biochemical reaction cartridge 1 is manipulated singly.

Figure 25:
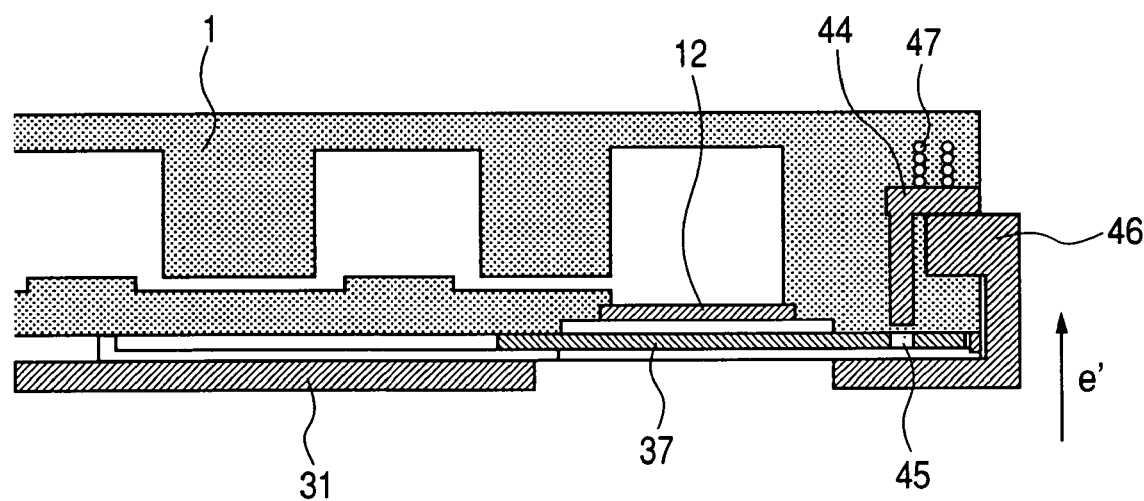
FIG. 25 is a diagram showing sections of the biochemical reaction cartridge and the carriage according to Example 5.

FIG. 25 illustrates a state in which the biochemical reaction cartridge 1 is placed in the carriage 31. A slit (not shown) is made near the lock pin 44 on the box of the biochemical reaction cartridge 1. Simultaneously with the placement of the biochemical reaction cartridge 1 in the carriage 31, the lock lever 46 provided in the carriage 31 enters the slit. The lock pin 44 is pushed upward in the direction of the arrow e' in FIG. 25 to thereby unlock the lock of the shutter 37.

As described above, the present invention has completely eliminated the possibility that an examiner unintentionally touches a site of a biochemical reaction cartridge required for the detection of target DNA in a sample with probes or other sites functionally required for the cartridge during the handling of the cartridge and the possibility of exposing these sites to the air before the detection of target DNA in a sample with probes. Accordingly, the present invention has completely eliminated the contamination of the sites with stains from hands and has almost eliminated the contamination of the sites with dirt and so on in the air. In addition, particularly for a fluorescently detecting biochemical reaction cartridge, the present invention has been capable of preventing the progression of deterioration of a fluorescent dye caused by the exposure of a DNA microarray portion to light. In summary, the present invention has allowed the accurate detection of target DNA in a sample with probes.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2004-319221 filed Nov. 2, 2004, which is hereby incorporated by reference herein.

What is claimed is:

1. A biochemical reaction cartridge comprising:
    a cartridge body having a portion of a reaction chamber for performing detection reaction of a target substance;
    a plate having a frontside comprising another portion of wall of the reaction chamber, and backside comprising a face for transmitting light from the reaction chamber, wherein said plate is composed of a material that transmits light therethrough;
    a covering shutter arranged on the cartridge body to move between at least a first position and a second position to allow a backside the face of the plate to be placed in an unexposed state and an exposed state, respectively;
    a shutter cover for attaching the covering shutter to the cartridge body and for sliding the covering shutter laterally with respect to the cartridge body, wherein said covering shutter comprising a material that does not transmit light therethrough; and
    a measurement error preventing means comprising at least one of the following:
        a display window adapted to allow an operator to recognize that the biochemical reaction cartridge is unavailable, a cover adapted to prohibit the sample from being injected into a sample inlet of the biochemical reaction cartridge, and a spring hinge adapted to prohibit the biochemical reaction cartridge from being placed in biochemical treatment equipment.

2. The biochemical reaction cartridge according to claim 1, further comprising a lock mechanism adapted to restrict motion of the covering shutter, wherein the lock is unlocked simultaneously with or after placement of the biochemical reaction cartridge in biochemical treatment equipment.

3. A biochemical reaction cartridge according to claim 1, wherein the plate is a microarray.

4. A detection method using a biochemical reaction cartridge comprising a cartridge body having a portion of a reaction chamber for performing detection reaction of a target substance and a plate having a frontside comprising another portion of wall of the reaction chamber, and a backside comprising a face for transmitting light from the reaction chamber, wherein said plate is composed of a material that passes light therethrough, and a covering shutter arranged on the cartridge body to move between at least a first position and a second position to allow a backside the face of the plate to be placed in an unexposed state and an exposed state, respectively, and a shutter cover for attaching the covering shutter to the cartridge body and for sliding the covering shutter laterally with respect to the cartridge body, wherein said covering shutter comprising a material that does not transmit light therethrough, the detection method comprising the steps of:
  installing a DNA plate;
  providing the covering shutter that prevents the backside of the plate from coming into contact with the outside;
  mounting the biochemical reaction cartridge on biochemical treatment equipment;
  then unlocking the covering shutter of the biochemical reaction cartridge; and
  detecting the reaction of a target substance on the plate by passing light through the reaction chamber.

5. The method according to claim 4, wherein the plate is a microarray.

* * * * *